(12) United States Patent
Honkonen et al.

(10) Patent No.: US 6,698,423 B1
(45) Date of Patent: Mar. 2, 2004

(54) METHODS AND APPARATUS TO GENERATE LIQUID AMBULATORY OXYGEN FROM AN OXYGEN CONCENTRATOR

(75) Inventors: Scott C. Honkonen, San Diego, CA (US); Theodore B. Hill, San Diego, CA (US); Charles C. Hill, Del Mar, CA (US); Graham Walker, Nanaimo (CA)

(73) Assignees: SeQual Technologies, Inc., San Diego, CA (US); Teijin Limited, Osaka (JP)

( * ) Notice: Subject to any disclaimer, the term of this patent is extended or adjusted under 35 U.S.C. 154(b) by 0 days.

(21) Appl. No.: 09/420,892

(22) Filed: Oct. 19, 1999

Related U.S. Application Data

(63) Continuation-in-part of application No. 08/876,970, filed on Jun. 16, 1997, now Pat. No. 5,979,440.

(51) Int. Cl.⁷ .................................................. A62B 7/06
(52) U.S. Cl. ........................ 128/201.21; 128/200.24; 128/204.15; 128/204.17
(58) Field of Search ............... 62/606, 615; 162/110, 162/174; 128/200.24, 201.21, 204.15, 204.17

(56) References Cited

U.S. PATENT DOCUMENTS

| | | | | |
|---|---|---|---|---|
| 609,499 A | * | 8/1898 | Chatwood et al. | 122/485 |
| 621,536 A | * | 3/1899 | Ostergren et al. | 62/615 |
| 621,537 A | * | 3/1899 | Ostergren et al. | 62/615 |
| 665,912 A | * | 1/1901 | Jolicard | 122/501 |
| 707,633 A | * | 8/1902 | Place | 62/615 |
| 718,572 A | * | 1/1903 | Joly | 62/615 |
| 879,302 A | * | 2/1908 | Nesmith | 138/38 |
| 881,176 A | * | 3/1908 | Claude | 62/615 |
| 948,835 A | * | 2/1910 | Walter | 165/160 |
| 1,454,053 A | * | 5/1923 | Jones | 165/161 |
| 1,782,409 A | * | 11/1930 | Chute | 165/161 |
| 1,796,510 A | * | 3/1931 | Delas et al. | 165/160 |
| 1,821,080 A | * | 9/1931 | Sprong | 165/183 |
| 1,867,163 A | * | 7/1932 | Loebell | 165/161 |
| 1,957,006 A | * | 5/1934 | Wescott | 165/110 |
| 2,017,676 A | * | 10/1935 | Girsewald et al. | 165/104.19 |
| 2,194,654 A | * | 3/1940 | Hadamovsky | 62/606 |
| 2,210,031 A | * | 8/1940 | Greene | 62/117 |

(List continued on next page.)

OTHER PUBLICATIONS

"Hautkondensation an feingewelten Oberflachen bei Beruckischtigun der Obrflachenspannungen"; Von Romano Gregoric, vol. V, 1954 (in German).

"Design Manual for Two–Phase Components of Spacecraft Thermal Management Systems"; PL–TR–92–3002, Crowley et al, Phillips Laboratory, Sep., 1992.

*Primary Examiner*—Aaron J. Lewis
(74) *Attorney, Agent, or Firm*—Procopio, Cory, Hargreaves & Savitch, LLP

(57) ABSTRACT

The present invention is directed to a much safer and less expensive way of providing portable oxygen from a gas concentrator for patients who do not want to be tied to a stationary machine or restricted by present oxygen technology. The present invention involves a home liquid oxygen ambulatory system for supplying a portable supply of oxygen, where a portion of the gaseous oxygen output obtained from an oxygen concentrator is condensed into liquid oxygen. The system includes an oxygen concentrator which separates oxygen gas from the ambient air, a condenser in communication with the oxygen concentrator for receiving and liquefying the oxygen gas flow, a cryocooler associated with the condenser, and a first storage dewar in fluid communication with the condenser and adapted to store the oxygen liquefied by the condenser, the first storage dewar including means for transferring liquid oxygen from the first dewar to a second dewar for storing a quantity of oxygen suitable for moveable oxygen treatment.

30 Claims, 21 Drawing Sheets

U.S. PATENT DOCUMENTS

| | | | | |
|---|---|---|---|---|
| 2,318,206 A | * | 5/1943 | Eisenlohr | 138/37 |
| 2,384,714 A | * | 9/1945 | Villiger | 165/161 |
| 2,434,519 A | * | 1/1948 | Raskin | 165/110 |
| 2,440,245 A | * | 4/1948 | Chevigny | 165/80.4 |
| 2,751,199 A | * | 6/1956 | Williams | 165/47 |
| 2,797,554 A | * | 7/1957 | Donovan | 62/509 |
| 2,905,447 A | * | 9/1959 | Huet | 165/165 |
| 2,937,079 A | * | 5/1960 | Pool | 422/201 |
| 2,943,454 A | * | 7/1960 | Lewis | 62/50.5 |
| 2,945,354 A | * | 7/1960 | Moskowitz | 62/50.2 |
| 2,958,204 A | * | 11/1960 | Spaulding | 62/48.1 |
| 2,960,834 A | * | 11/1960 | Patrick | 62/7 |
| 2,964,919 A | * | 12/1960 | Howlett | 62/50.4 |
| 2,969,957 A | * | 1/1961 | Beurtheret | 62/259.2 |
| 2,970,452 A | * | 2/1961 | Beckman et al. | 62/50.2 |
| 2,993,682 A | * | 7/1961 | Huet | 165/110 |
| 3,055,643 A | * | 9/1962 | Beurtheret | 165/110 |
| 3,097,497 A | * | 7/1963 | Fitt | 62/50.4 |
| 3,117,426 A | * | 1/1964 | Fischer et al. | 62/223 |
| 3,152,589 A | * | 10/1964 | Kugler | 128/201.21 |
| 3,183,678 A | * | 5/1965 | Hosford | 62/50.4 |
| 3,186,406 A | * | 6/1965 | Fitt et al. | 128/201.21 |
| 3,199,303 A | * | 8/1965 | Haumann et al. | 62/48.1 |
| 3,205,670 A | * | 9/1965 | Carolan | 62/50.4 |
| 3,318,307 A | * | 5/1967 | Nicastro | 128/201.21 |
| 3,354,664 A | * | 11/1967 | Van Der Ster et al. | 62/606 |
| 3,400,758 A | * | 9/1968 | Man Suk Lee | 165/159 |
| 3,570,481 A | * | 3/1971 | Woodberry, Jr. | 128/201.21 |
| 3,572,048 A | * | 3/1971 | Murphy | 62/50.2 |
| 3,707,078 A | * | 12/1972 | Cramer | 62/50.4 |
| 3,749,155 A | * | 7/1973 | Buffiere | 165/147 |
| 3,797,262 A | * | 3/1974 | Eigenbrod | 62/48.1 |
| 3,864,928 A | * | 2/1975 | Eigenbrod | 62/48.1 |
| 3,983,861 A | * | 10/1976 | Beauchaine | 126/656 |
| 4,211,086 A | * | 7/1980 | Leonard et al. | 62/48.1 |
| 4,253,519 A | * | 3/1981 | Kun et al. | 165/110 |
| 4,360,059 A | * | 11/1982 | Funke | 165/160 |
| 4,493,368 A | * | 1/1985 | Gronnerud et al. | 165/159 |
| 4,513,587 A | * | 4/1985 | Humpolik et al. | 62/515 |
| 4,848,447 A | * | 7/1989 | Sladky | 165/118 |
| 4,850,426 A | * | 7/1989 | Fayolle et al. | 165/111 |
| 4,899,810 A | * | 2/1990 | Fredley | 165/41 |
| 5,048,600 A | * | 9/1991 | Stout et al. | 165/110 |
| 5,454,429 A | * | 10/1995 | Neurauter | 165/109.1 |
| 5,458,190 A | * | 10/1995 | Sasaki et al. | 165/110 |
| 5,634,517 A | * | 6/1997 | Linden et al. | 165/111 |
| 5,697,228 A | * | 12/1997 | Paige | 62/615 |
| 5,893,275 A | * | 4/1999 | Henry | 62/615 |
| 5,979,440 A | * | 11/1999 | Honkonen et al. | 128/201.21 |
| 6,029,473 A | * | 2/2000 | Bravais | 62/606 |
| 6,212,904 B1 | * | 4/2001 | Arkharov et al. | 62/615 |
| 6,230,518 B1 | * | 5/2001 | Hahn et al. | 62/615 |
| 6,289,981 B1 | * | 9/2001 | Tokizaki et al. | 165/177 |
| 6,530,421 B1 | * | 3/2003 | Filius et al. | 165/109.1 |

* cited by examiner

TEMPERATURE – COMPOSITION DIAGRAM
FOR OXYGEN – ARGON MIXTURES

TEMPERATURE COMPOSITION DIAGRAM
FOR NITROGEN OXYGEN MIXTURES

CONTROL BLOCK DIAGRAM

Fig. 8
START-UP MODE
INPUT LEVELS & OUTPUT STATES

| INPUT | LEVEL | OUTPUT | STATE |
|---|---|---|---|
| OXYGEN SENSOR<br>LIQUID LEVEL SENSOR | >88%<br>0% | VALVE 19<br>VALVE 25<br>HEATER<br>CRYOCOOLER<br>INDICATOR | OPEN<br>OPEN/CLOSED *<br>OFF<br>ON<br>COOLDOWN |

\* MODULATED TO CONTROL PRESSURE

Fig. 9
CONDENSE MODE
INPUT LEVELS & OUTPUT STATES

| INPUT | LEVEL | OUTPUT | STATE |
|---|---|---|---|
| OXYGEN SENSOR<br>LIQUID LEVEL SENSOR | >88%<br><100% | VALVE 19<br>VALVE 25<br>HEATER<br>CRYOCOOLER<br>INDICATOR | OPEN<br>OPEN<br>OFF<br>ON<br>CONDENSE |
| OXYGEN SENSOR<br>LIQUID LEVEL SENSOR | ≤88%<br><100% | VALVE 19<br>VALVE 25<br>HEATER<br>CRYOCOOLER<br>INDICATOR | CLOSED<br>OPEN<br>OFF<br>OFF<br>$O_2$ LOW |
| OXYGEN SENSOR<br>LIQUID LEVEL SENSOR | >88%<br>≥100% | VALVE 19<br>VALVE 25<br>HEATER<br>CRYOCOOLER<br>INDICATOR | CLOSED<br>OPEN<br>OFF<br>OFF<br>FULL |

Fig. 10
TRANSFER MODE
INPUT LEVELS & OUTPUT STATES

| INPUT | LEVEL | OUTPUT | STATE |
|---|---|---|---|
| OXYGEN SENSOR<br>LIQUID LEVEL SENSOR | 20-95%<br><20% | VALVE 19<br>VALVE 25<br>HEATER<br>CRYOCOOLER<br>INDICATOR | CLOSED<br>OPEN<br>OFF<br>OFF<br>LIQ. LOW |
| OXYGEN SENSOR<br>LIQUID LEVEL SENSOR<br>PRESSURE SENSOR | 20-95%<br>≥20%<br><18 PSIG | VALVE 19<br>VALVE 25<br>HEATER<br>CRYOCOOLER<br>INDICATOR | CLOSED<br>CLOSED<br>ON<br>OFF<br>WAIT |
| OXYGEN SENSOR<br>LIQUID LEVEL SENSOR<br>PRESSURE SENSOR | 20-95%<br>≥20%<br>>18 PSIG | VALVE 19<br>VALVE 25<br>HEATER<br>CRYOCOOLER<br>INDICATOR | CLOSED<br>CLOSED<br>ON<br>OFF<br>TRANSFER |
| OXYGEN SENSOR<br>LIQUID LEVEL SENSOR<br>PRESSURE SENSOR | 20-95%<br>≥20%<br>>22 PSIG | VALVE 19<br>VALVE 25<br>HEATER<br>CRYOCOOLER<br>INDICATOR | CLOSED<br>CLOSED<br>OFF<br>OFF<br>TRANSFER |

Fig. 11
BOIL-DRY MODE
INPUT LEVELS & OUTPUT STATES

| INPUT | LEVEL | OUTPUT | STATE |
|---|---|---|---|
| OXYGEN SENSOR<br>LIQUID LEVEL SENSOR<br>TEMPERATURE SENSOR | 20-95%<br><100%<br><300K | VALVE 19<br>VALVE 25<br>HEATER<br>CRYOCOOLER<br>INDICATOR | CLOSED<br>OPEN<br>ON<br>OFF<br>BOIL-DRY |
| OXYGEN SENSOR<br>LIQUID LEVEL SENSOR<br>TEMPERATURE SENSOR | 20-95%<br>0-100%<br>≥300K | VALVE 19<br>VALVE 25<br>HEATER<br>CRYOCOOLER<br>INDICATOR | CLOSED<br>OPEN<br>OFF<br>OFF<br>WARM |

METHODS AND APPARATUS TO GENERATE LIQUID AMBULATORY OXYGEN FROM AN OXYGEN CONCENTRATOR

PRIOR APPLICATIONS

This application is a continuation-in-part of U.S. patent application Ser. No. 08/876,970, filed Jun. 16, 1997 now U.S. Pat. No. 5,979,440.

BACKGROUND OF THE INVENTION

The field of this invention relates to using an oxygen concentrator to create a portable supply of supplementary oxygen for ambulatory respiratory patients so that they can lead normal and productive lives—as the typical primary oxygen sources are too bulky to carry or require excessive power to operate.

There is a burgeoning need for home and ambulatory oxygen. Supplemental oxygen is necessary for patients suffering from lung disorders; for example, pulmonary fibrosis, sarcoidosis, or occupational lung disease. For such patients, oxygen therapy is an increasingly beneficial, life-giving development. While not a cure for lung disease, supplemental oxygen increases blood oxygenation, which reverses hypoxemia. This therapy prevents long-term effects of oxygen deficiency on organ systems—in particular, the heart, brain and kidneys. Oxygen treatment is also prescribed for Chronic Obstructive Pulmonary Disease (COPD), which afflicts about 25 million people in the U.S., and for other ailments that weaken the respiratory system, such as heart disease and AIDS. Supplemental oxygen therapy is also prescribed for asthma and emphysema.

The normal prescription for COPD patients requires supplemental oxygen flow via nasal cannula or mask twenty four hours per day. The average patient prescription is two liters per minute of high concentration oxygen to increase the oxygen level of the total air inspired by the patient from the normal 21% to about 40%. While the average oxygen flow requirement is two liters per minute, the average oxygen concentrator has a capacity of four to six liters of oxygen per minute. This extra capacity is occasionally necessary for certain patients who have developed more severe problems but they are not generally able to leave the home (as ambulatory patients) and do not require a portable oxygen supply.

There are currently three modalities for supplemental medical oxygen: high pressure gas cylinders, cryogenic liquid in vacuum insulated containers or thermos bottles commonly called "dewars," and oxygen concentrators. Some patients require in-home oxygen only while others require in-home as well as ambulatory oxygen depending on their prescription. All three modalities are used for in-home use, although oxygen concentrators are preferred because they do not require dewar refilling or exchange of empty cylinders with full ones.

Only small high pressure gas bottles and small liquid dewars are portable enough to be used for ambulatory needs (outside the home). Either modality may be used for both in-home and ambulatory use or may be combined with an oxygen concentrator which would provide in-home use.

As we describe below, the above-described current methods and apparatus have proven cumbersome and unwieldy and there has been a long-felt need for improved means to supply the demand for portable/ambulatory oxygen.

For people who need to have oxygen but who need to operate away from an oxygen-generating or oxygen-storage source such as a stationary oxygen system (or even a portable system which cannot be easily carried), the two most prescribed options generally available to patients are: (a) to carry with them small cylinders typically in a wheeled stroller; and (b) to carry portable containers typically on a shoulder sling. Both these gaseous oxygen and liquid oxygen options have substantial drawbacks. But from a medical view, both have the ability to increase the productive life of a patient.

The major drawback of the gaseous oxygen option is that the small cylinders of gaseous oxygen can only provide gas for a short duration. Oxygen conserving devices that limit the flow of oxygen to the time of inhalation may be used. However, the conserving devices add to the cost of the service and providers have been reluctant to add it because there often is no health insurance reimbursement. Indeed, the insurance reimbursement for medical oxygen treatment appears to be shrinking.

Another drawback of the gaseous oxygen option is the source of or refill requirement for oxygen once the oxygen has been depleted from the cylinder. These small gas cylinders must be picked up and refilled by the home care provider at a specialized facility. This requires regular visits to a patient's home by a provider and a substantial investment in small cylinders for the provider because so many are left at the patient's home and refilling facility. Although it is technically possible to refill these cylinders in the patient's home using a commercial oxygen concentrator that extracts oxygen from the air, this task would typically require an on-site oxygen compressor to boost the output pressure of the concentrator to a high level in order to fill the cylinders. Additionally, attempting to compress the oxygen in pressurized canisters in the home is dangerous, especially for untrained people. This approach of course presents several safety concerns for in-home use. For example, in order to put enough of this gas in a portable container, it must typically be compressed to high pressure (~2000 psi). Compressing oxygen from 5 psi (the typical output of an oxygen concentrator) to 2000 psi will produce a large amount of heat. (Enough to raise the temperature 165° C. per stage based on three adiabatic compression stages with intercooling.) This heat, combined with the oxygen which becomes more reactive at higher pressures, sets up a potential combustion hazard in the compressor in the patient's home. Thus, utilizing and storing a high pressure gas system in the patient's home is dangerous and not a practical solution.

The convenience and safety issues are not the only drawbacks of this compressed oxygen approach. Another drawback is that the compressors or pressure boosters needed are costly because they require special care and materials needed for high pressure oxygen compatibility. For example, a Rix Industries, Benicia, Calif., ⅓ hp unit costs about $10,000 while a Haskel International, Burbank, Calif., air-powered booster costs about $2200 in addition to requiring a compressed air supply to drive it. Litton Industries and others also make oxygen pressure boosters.

Turning now to the liquid oxygen storage option, its main drawback is that it requires a base reservoir—a stationary reservoir base unit about the size of a standard beer keg—which has to be refilled about once a week. The liquid oxygen can then be obtained from a base unit and transferred to portable dewars which can be used by ambulatory patients. Also, with the liquid oxygen option, there is substantial waste, as a certain amount of oxygen is lost during the transfer to the portable containers and from evaporation. It is estimated that 20% of the entire contents of the base cylinder will be lost in the course of two weeks because of losses in transfer and normal evaporation. These units will typically boil dry over a period of 30 to 60 days even if no oxygen is withdrawn.

There are other complications. Typically, supplemental oxygen is supplied to the patient by a home care provider, in exchange for which it receives a fixed monetary payment from insurance companies or Medicare regardless of the modality. Oxygen concentrators for use in the home are preferred and are the least expensive option for the home care provider. For outside the home use however, only small high pressure gas bottles and small liquid dewars are portable enough to be used for ambulatory needs. One of these two modalities may be used for both in-home and ambulatory use or may be combined with an oxygen concentrator which would provide in-home use. In either case, the home care provider must make costly weekly or biweekly trips to the patient's home to replenish the oxygen. One of the objects of this invention is to eliminate these costly "milk runs."

Portable oxygen concentrators are commercially available for providing patients with gaseous oxygen. These devices are "portable" solely in the sense that they can be carried to another point of use such as in an automobile or in an airplane. At present, there are no home oxygen concentrators commercially available that can provide liquid oxygen. One type of medical oxygen concentrator takes in air and passes it through a molecular sieve bed, operating on a pressure swing adsorption cycle, which strips most of the nitrogen out, producing a stream of ~90% oxygen, for example, as shown in U.S. Pat. Nos. 4,826,510 and 4,971,609 (which are incorporated herein by reference). While, as set out in the Information Disclosure Statement, complex oxygen liquefaction systems have been disclosed for use by the military in jet aircraft, and while large-scale commercial plants have been disclosed, this technology has not yet found its way into the home to help individual patients and to benefit the general public. A truly portable oxygen concentrator has not yet been perfected and this event is unlikely, at least in the near future, because the power requirements are too large to be provided by a lightweight battery pack.

Since liquid oxygen requires periodic delivery and home oxygen concentrators are not commercially available that would create liquid oxygen, there has existed a long-felt need for a device or method having the capability to concentrate oxygen from the air, liquefy it, and transfer it into portable dewars in a home environment, and for a home oxygen concentrator unit which allows excess flow capacity from the concentrator to be stored by either compression or liquefaction for later use.

SUMMARY OF THE INVENTION

An aspect of the present invention involves a home liquid oxygen ambulatory system for supplying a portable supply of oxygen, where a portion of the gaseous oxygen output obtained from an oxygen concentrator is condensed into liquid oxygen. The system includes an oxygen concentrator which separates oxygen gas from the ambient air, a condenser in communication with the oxygen concentrator for receiving and liquefying the oxygen gas flow, a cryocooler associated with the condenser, and a first storage dewar in fluid communication with the condenser and adapted to store the oxygen liquefied by the condenser, the first storage dewar including means for transferring liquid oxygen from the first dewar to a second dewar for storing a quantity of oxygen suitable for moveable oxygen treatment.

In an embodiment of the above aspect of the invention, the liquid oxygen transferring means is adapted to increase the pressure in the first dewar.

In a further embodiment of the above aspect of the invention, the liquid transferring means includes a heater immersed within the liquid oxygen in the first dewar.

In a still further embodiment of the above aspect of the invention, the first dewar includes an inner vessel in which the liquid oxygen reside, and liquid transferring means includes a heater attached to the outer surface of inner vessel.

In another embodiment of the above aspect of the invention, the condenser is in communication with the concentrator through a line, and the liquid transferring means includes a compressor located in the line between the condenser and the concentrator.

In an additional embodiment of the above aspect of the invention, the liquid transferring means includes a high-pressure compressor in communication with the concentrator for delivering high-pressure air thereto.

In another embodiment of the above aspect of the invention, the liquid transferring means includes a vaporizer loop associated with the first dewar.

In a further embodiment of the above aspect of the invention, the liquid transferring means includes a controllable heat leak associated with the first dewar.

In a still further embodiment of the above aspect of the invention, the liquid transferring means includes a gravity-assisted dispensing mechanism.

In an additional embodiment of the above aspect of the invention, the system further includes the second storage dewar and the second storage dewar is adapted to be filled at a pressure below 20 psig.

An additional aspect of the invention involves a home liquid oxygen ambulatory system for supplying a portable supply of oxygen, where a portion of the gaseous oxygen output obtained from an oxygen concentrator is condensed into liquid oxygen. The system includes an oxygen concentrator which separates oxygen gas from the ambient air, a condenser in communication with the oxygen concentrator for receiving and liquefying the oxygen gas flow, a cryocooler associated with the condenser, and a portable dewar adapted to interface with the condenser and adapted to store the oxygen liquefied by the condenser.

Another aspect of the present invention involves a method for generating liquid oxygen in a home from a home liquid oxygen ambulatory system having an oxygen concentrator, a condenser, and cryocooler, a storage dewar and means for transferring liquid oxygen from the first dewar to a second dewar. The method includes generating a gaseous supply of oxygen using the oxygen concentrator; splitting off at least a portion of the gaseous supply to be liquefied; cooling the supply of oxygen using the condenser and cryocooler to transform the gaseous oxygen to liquid oxygen; storing the liquid oxygen in the storage dewar; and transferring the liquid oxygen in the storage dewar with the liquid oxygen transferring means to a second dewar for storing a quantity of liquid oxygen from which smaller quantities can be transferred for moveable oxygen treatment.

In an embodiment of the above aspect of the invention, transferring the liquid oxygen includes increasing the pressure in the first dewar.

In an additional embodiment of the above aspect of the invention, the liquid transferring means includes a heater immersed within the liquid oxygen in the first dewar and transferring the liquid oxygen includes heating the liquid oxygen in the first dewar so that the pressure is increased in the first dewar.

In another embodiment of the above aspect of the invention, the first dewar includes an inner vessel in which the liquid oxygen reside, the liquid transferring means includes a heater attached to the outer surface of inner vessel, and transferring the liquid oxygen includes heating the liquid oxygen in the first dewar so that the pressure is increased in the first dewar.

In a further embodiment of the above aspect of the invention, the condenser is in communication with the concentrator through a line, and the liquid transferring means includes a compressor located in the line between the condenser and the concentrator, and transferring the liquid oxygen includes increasing the pressure of gaseous oxygen entering the condenser and the dewar with the compressor.

In a still further embodiment of the above aspect of the invention, the liquid transferring means includes a high-pressure compressor in communication with the concentrator for delivering high-pressure air thereto, and transferring the liquid oxygen includes increasing the pressure of gaseous oxygen entering the condenser and the dewar with the compressor.

In an additional embodiment of the above aspect of the invention, the liquid transferring means includes a vaporizer loop associated with the first dewar, and transferring the liquid oxygen includes heating the liquid oxygen in the first dewar with the vaporizer loop so that the pressure is increased in the first dewar.

In another embodiment of the above aspect of the invention, the liquid transferring means includes a controllable heat leak associated with the first dewar, and transferring the liquid oxygen includes heating the liquid oxygen in the first dewar so that the pressure is increased in the first dewar.

In a further embodiment of the above aspect of the invention, the liquid transferring means includes a gravity-assisted dispensing mechanism.

In a still further embodiment of the above aspect of the invention, the system further includes the second storage dewar, the second storage dewar is adapted to filled at a pressure below 20 psig.

Another aspect of the present invention involves a liquefier for a home liquid oxygen ambulatory system that is resistant to plugging. The home liquid oxygen ambulatory system includes an oxygen concentrator for delivering gaseous flow to the liquefier and a storage dewar having an inner vessel for storing liquid oxygen produced by the liquefier. The liquefier includes a condenser, a refrigerating device associated with the condenser, means for communicating incoming gaseous flow from the oxygen concentrator to the condenser, the communicating means having an inner surface with a dimension D, means for venting gaseous flow not condensed from the inner vessel, the venting means having an outer surface with an dimension d, and whereby the dimension D of the inner surface of the communicating means is significantly larger than the dimension d of the outer surface of the venting means to allow for the build-up of solid contaminants on the outer surface of the venting means without plugging up the communicating means.

In an embodiment of the above aspect of the invention, the venting means includes a recuperator comprised of a helical coil of tubing, the tubing having the outer surface with a diameter of the dimension d, whereby the incoming gas stream flows over the outer surface of the helical coil of tubing and a vent stream flows inside the helical coil of tubing.

In another embodiment of the above aspect of the invention, the outer surface of the helical coil of tubing has a cold surface to freeze out trace impurities of solid contaminants such as $H_2O$, $CO_2$ and hydrocarbons.

In a further embodiment of the above aspect of the invention, the communicating means is comprised of a neck tube having the inner surface with a diameter of the dimension D.

In a still further embodiment of the above aspect of the invention, the liquefier further includes a liquid withdrawal tube located central to the refrigerating device, recuperator and condenser for removing liquid oxygen from the storage dewar.

In an additional embodiment of the above aspect of the invention, the refrigerating device is integral with the condenser.

In another embodiment of the above aspect of the invention, the refrigerating device, condenser and recuperator are integral with the storage dewar.

Another aspect of the invention involves a method for generating liquid oxygen in a home from a home liquid oxygen ambulatory system having an oxygen concentrator, a condenser, a cryocooler, a recuperator and a storage dewar. The method includes generating a gaseous supply of oxygen, which includes some trace impurities, using the oxygen concentrator; splitting off at least a portion of the gaseous supply to be liquefied; cooling the supply of oxygen using the condenser and cryocooler to transform the gaseous oxygen to liquid oxygen; condensing less than all of the gaseous oxygen supply flowing into the condenser; freezing out the trace impurities of the gaseous supply of oxygen and venting the non-condensed nitrogen, argon and oxygen with the recuperator; storing the liquid oxygen in the storage dewar; and periodically removing accumulated frozen impurities on the recuperator by boiling-off any stored liquid oxygen and then flow purging the system until the system has reached room temperature.

Another aspect of the invention involves a generally vertically oriented, gravity assisted condenser for use with a refrigerating device to liquefy gaseous oxygen in a home liquid oxygen ambulatory system. The condenser includes a generally vertically oriented tubular member adapted to conduct heat axially to the refrigerating device, the tubular member having outer and inner surfaces, at least one of the outer and inner surfaces having a plurality of generally vertically oriented flutes and convex fins adapted to increase the condensation rate per unit area by thinning the liquid film and drain the condensate to keep the condensate from flooding the condensation surfaces.

In an embodiment of the above aspect of the invention, the fins have a hyperbolic cosine profile.

In an additional embodiment of the above aspect of the invention, the flutes have a profile selected from the group consisting of concave, generally V-shaped, generally rectilinear.

In another embodiment of the above aspect of the invention, the plurality of generally vertically oriented flutes and convex fins are located on both the outer and inner surfaces.

Another aspect of the invention involves a generally vertically oriented, gravity assisted condenser for use with a refrigerating device to liquefy gaseous oxygen in a home liquid oxygen ambulatory system. The condenser includes a generally vertically oriented tubular member adapted to conduct heat axially to the refrigerating device, the tubular member having outer and inner surfaces, at least one of the outer and inner surfaces includes means for enhancing the condensation rate per unit area by maintaining a small liquid film thickness on the condensation surfaces.

In an embodiment of the above aspect of the invention, the condensation enhancing means includes a plurality of generally vertically oriented flutes and convex fins.

In an additional embodiment of the above aspect of the invention, the fins have a hyperbolic cosine profile.

In a further embodiment of the above aspect of the invention, the flutes have a profile selected from the group consisting of concave, generally V-shaped, generally rectilinear.

In a still further embodiment of the above aspect of the invention, the plurality of generally vertically oriented flutes and convex fins are located on both the outer and inner surfaces.

BRIEF DESCRIPTION OF THE DRAWINGS

FIG. 8 shows the controller input levels and output states for the start-up mode of the preferred embodiment.

FIG. 9 shows the controller input levels and output states for the condense mode of the preferred embodiment.

FIG. 10 shows the controller input levels and output states for the transfer mode of the preferred embodiment.

FIG. 11 shows the controller input levels and output state for the boil dry mode of the preferred embodiment.

DETAILED DESCRIPTION OF THE PREFERRED EMBODIMENT

Figure 1:
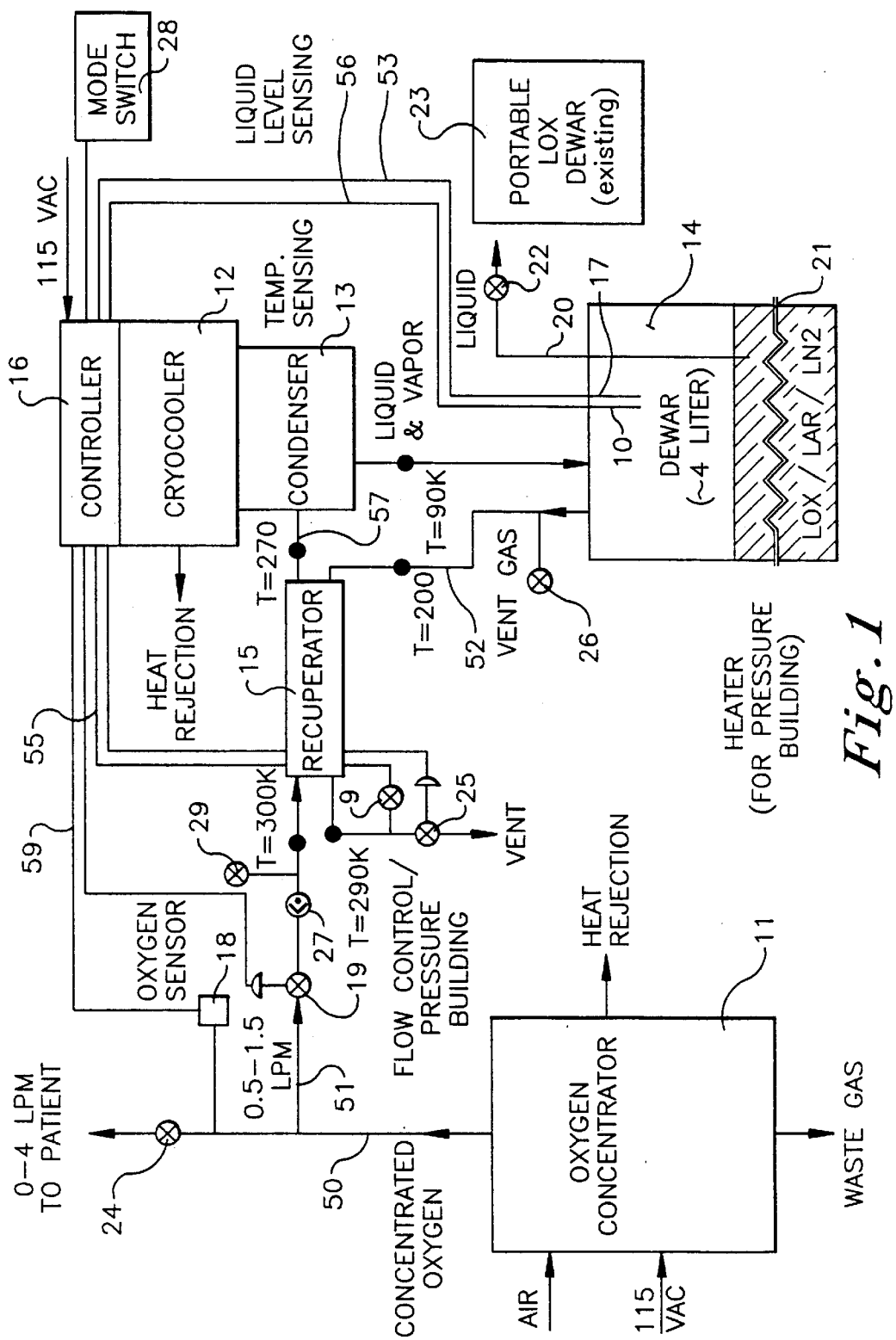
FIG. 1 is a block diagram of the invention in the medical oxygen preferred embodiment where gaseous oxygen is split off and liquefied for storage in a stationary dewar or container.

A flow chart of the preferred embodiment of the invention is set out in FIG. 1. Its main components include an oxygen concentrator 11, a cryocooler 12, a condenser 13, and a storage/collection dewar or vacuum insulated container 14. In the preferred embodiment, the oxygen concentrator 11 operates on a pressure swing adsorption cycle and essentially strips all or most of the nitrogen from air along with other minor components such as $H_2O$, $CO_2$, CO, $NO_x$, etc. The result is a stream of dry gas with high oxygen concentration (~92%) flowing in fluid outlet 50. A portion of the gas from this output in fluid outlet 50 is routed to a condenser 13 in association with a cryocooler (or cryogenic refrigerator) 12 through flow lines 51 and 57. The cryocooler provides cooling of the condenser heat exchanger 13 to liquefaction temperatures, causing the oxygen in contact therewith to go from the gaseous to the liquid phase. The condenser 13 typically must be insulated from ambient heating and may in practice even be located inside the dewar 14. In order to lessen the load on the cryocooler 12, a recuperator 15 may be used to pre-cool the incoming stream utilizing the vent flow through line 52 out of the dewar as a cooling medium. In practice, this recuperator 15 may also be located within the dewar 14 to reduce ambient heating.

Controller 16 may be equipped with a microprocessor, adequate memory, software and ancillary equipment comprising a computer which can be used to monitor and control the operation of the system. The controller 16 may be provided with signals from liquid level sensor 17, oxygen sensor 18, pressure transducer 9, and temperature sensor 10 via lines 53, 59, 55 and 56, respectively. These signals are sensed and processed by the computer, with the controller operating valve 19, valve 25, heater 21, and cryocooler 12, in accordance with predetermined programs.

The controller also provides output indicators for the patient. The liquid level in the dewar is continuously displayed and the patient is alerted when the oxygen concentration is low and when the system is ready for them to transfer liquid to a portable dewar. A modem or wireless link may be included to enable remote monitoring of the key parameters of the system by the home care provider as well as information which is useful for repair, maintenance, billing, and statistical studies of patients for the medical oxygenation market. Key system parameters of interest include the number of liquid transfers performed, the oxygen concentration history, number of run hours on the cryocooler, and time of the last boil-dry as well as number of boil dries performed. The controller may include a computer and/or a microprocessor located either integrally with the liquefaction system claimed herein or remotely therefrom but in communication therewith using either a modem and telephone lines or with a wireless interface. The computer and/or microprocessor may include memory having a database, or may be remotely connected to a memory or database using a network. An Optimal Liquefaction Schedule for optimal operation of the liquefaction system is set out in FIGS. 7–10 and may be stored in the controller using the memory and database. The controller can sense optimum parameters of the system and optimally control, including by activating servomechanisms, liquefaction and transfer of liquid oxygen.

Dewar 14 is equipped with a dip tube 20 and heater 21. Heater 21 is used to build pressure in the dewar in order to expel liquid out the dip tube 20 when so desired. A quick disconnect valve 22 or other flow control means is located on the end of the dip tube. This allows connection of a portable LOX dewar 23, which can then be carried by the patient requiring a mobile/ambulatory supply of oxygen.

Figure 2:
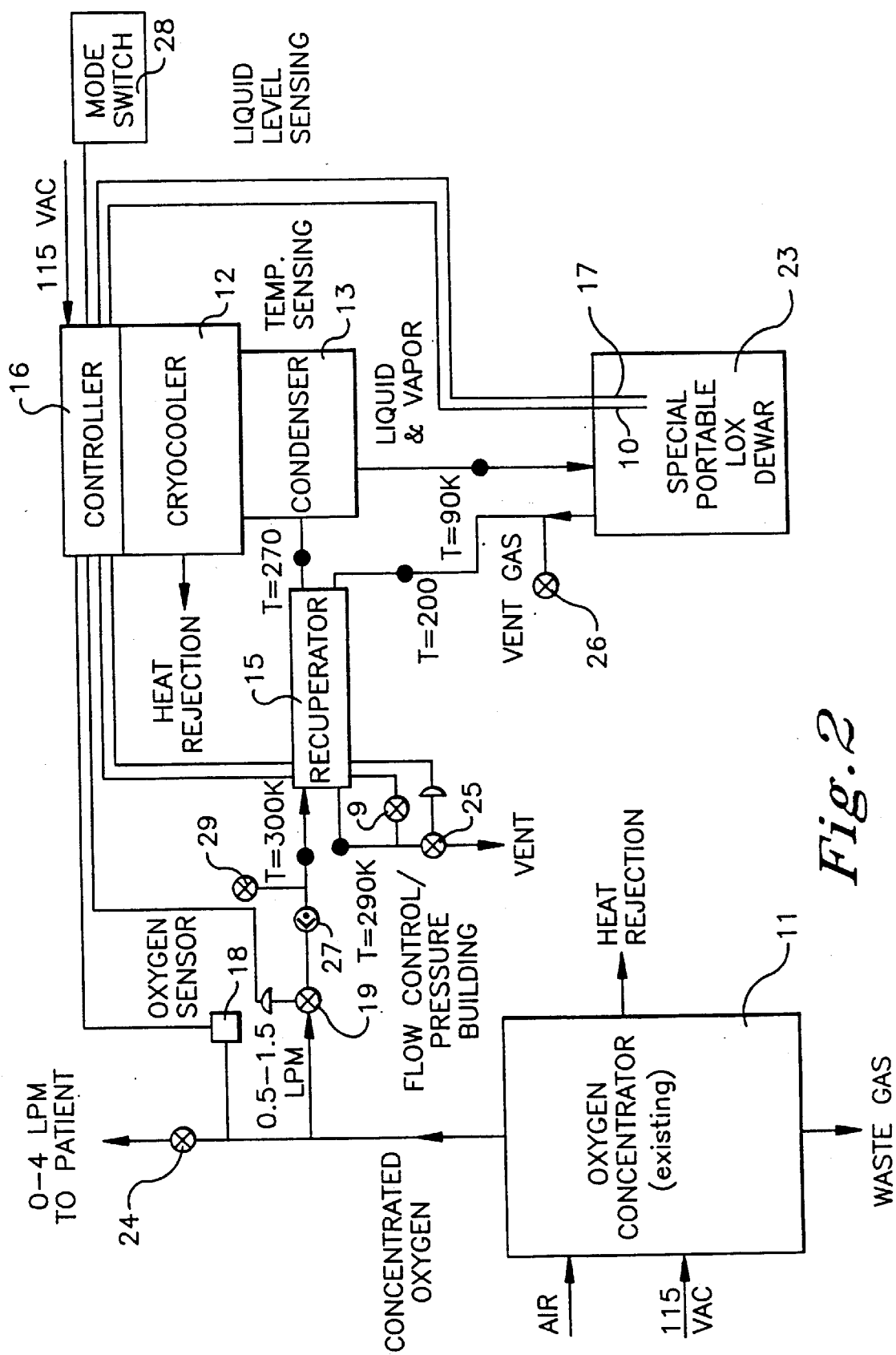
FIG. 2 shows another preferred embodiment of the invention for ambulatory supplemental oxygen using a portable LOX dewar.

In another embodiment of this system shown in FIG. 2, the dewar 14 could be eliminated and replaced with a portable dewar 23 which is modified slightly from those existing today. The new portable dewar would interface with the condenser 13, recuperator 15, and controller 16. This embodiment requires a slightly different control scheme from that given for the preferred embodiment as the transfer and boil-dry modes are eliminated. Any small amount of accumulated water and hydrocarbons are eliminated from the portable dewar 23 after each use by allowing it to warm to room temperature before reuse.

In operation, in the preferred embodiment of FIG. 1, where a pressure swing adsorption ("PSA") system is used, air is drawn into the oxygen concentrator 11, where it is compressed by an oilless compressor, cooled, and passed through molecular sieve beds operating on the pressure swing adsorption cycle, as shown in U.S. Pat. Nos. 5,366,541; 5,112,367; 5,268,021 and Re. 35,009, which are incorporated herein by reference. This PSA system produces a 5–6 liters per minute (LPM) gas stream with high oxygen concentration at 3–7 pounds per square inch gauge (psig). The composition of this gas stream varies but is typically 90–95% oxygen, 5–6% argon, 0–4% nitrogen, <15 parts per million (ppm) water vapor, and <1 ppm hydrocarbons. Exhaust from the PSA cycle (80–84% nitrogen, 15–19% oxygen, 0.6–0.8% argon, and trace amounts of water vapor, carbon dioxide and hydrocarbons) is vented into the atmosphere as waste gas. In the preferred embodiment, the high concentration oxygen stream in fluid outlet 50 is split with 0–4 lpm going through control valve 24, for patient consumption, and 0.5–1.5 lpm through line 51 and control valve 19 for liquefaction. Oxygen sensor 18, monitors the oxygen concentration produced by oxygen concentrator 11. If the oxygen concentration falls below 88%, controller 16 will close valve 19 and turn off the cryocooler 12.

Even though 88% oxygen is adequate as supplemental oxygen therapy, if this was liquefied, as will be described below, the initial revaporized stream may have a reduced oxygen content because of the close boiling points of the components of the mixture. The temperature of the split gas stream entering the recuperator 15 is about room temperature. It is cooled to about 270 K (or colder) by the vent gas from the dewar flowing through the other side of the recuperator via line 52. The recuperator 15 reduces the load on the cryocooler by using the cold vent gas to pre-cool the oxygen-rich gas stream flowing into the condenser 13. From the recuperator 15 the high oxygen concentration stream flows through a line 57 to the condenser 13, which is cooled to ~90 K by the cryocooler 12.

The condenser 13 provides cold surfaces to further cool and condense the flow. It is important to note that the gas passing through the condenser 13 is a mixture of oxygen, argon, and nitrogen. The normal boiling points of these components are: 90.18 K, 87.28 K, and 77.36 K respectively. Because of the close boiling points of the components of this mixture, there was initial skepticism because of the concern that all the nitrogen and argon would condense along with the oxygen. If this concern was realized, when this liquid mixture was revaporized, the lower boiling point components; i.e., nitrogen and argon, would boil off first, resulting in flow with high concentrations of nitrogen, argon and a much lower oxygen concentration than that which was supplied to the condenser—which would make the process of oxygen treatment ineffective or a failure.

Figure 3:
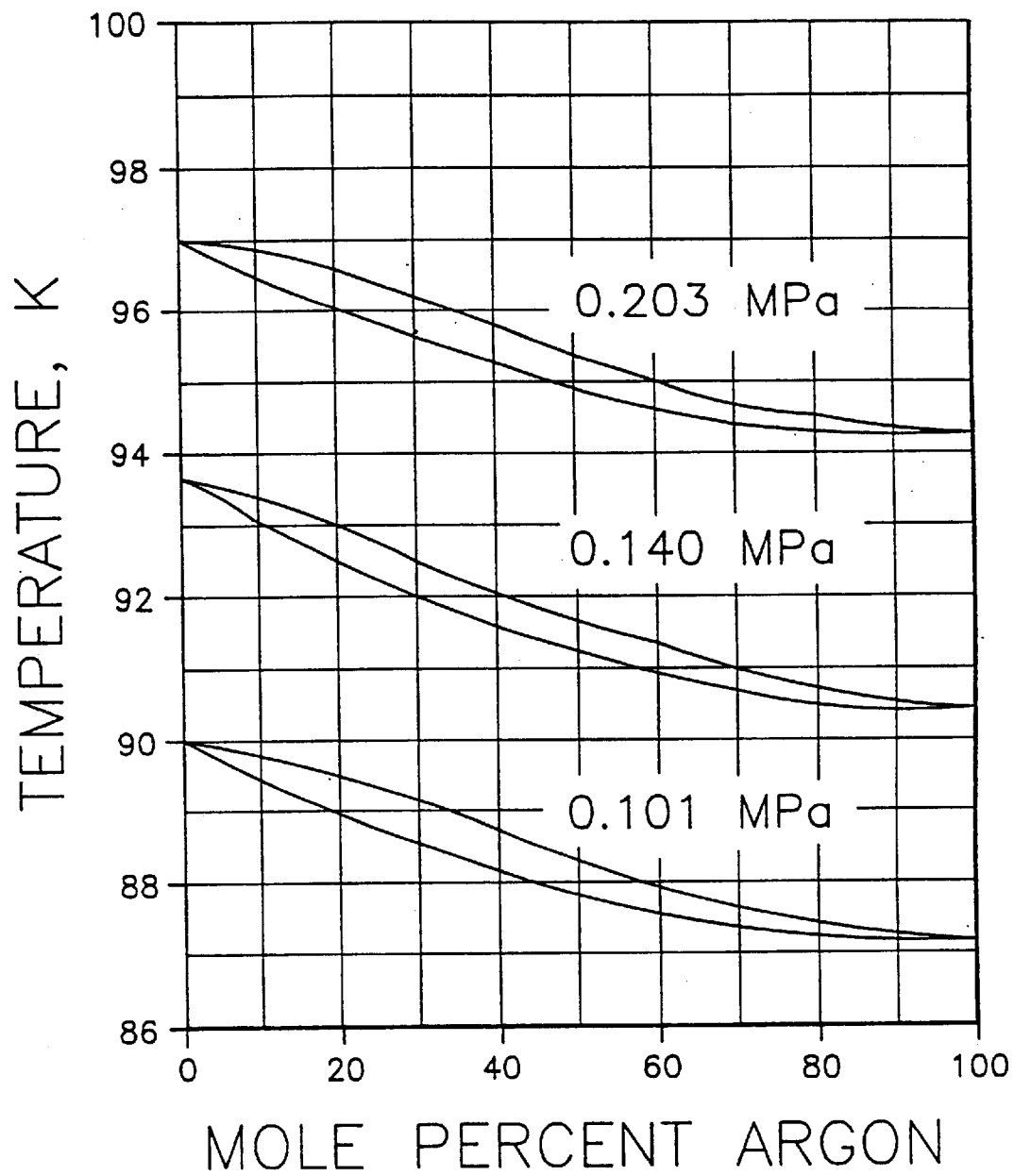
FIG. 3 shows a typical temperature-composition diagram for oxygen-argon mixtures at typical dewar pressures.
Figure 4:
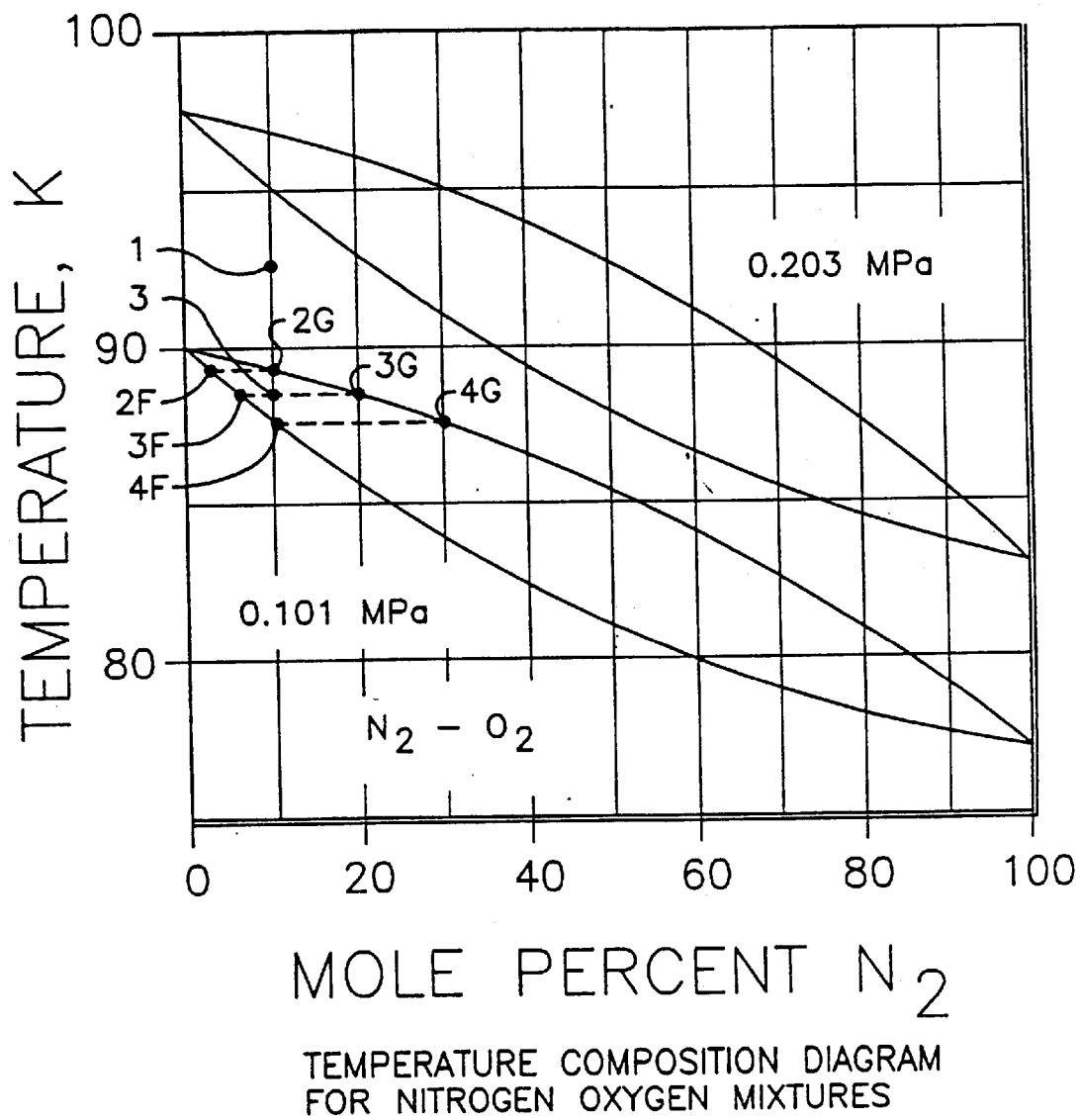
FIG. 4 shows a typical temperature-composition diagram for nitrogen-oxygen mixtures at typical dewar pressures.

This concern is explained in FIGS. 3 and 4 which are temperature composition diagrams for binary mixtures of oxygen-argon and oxygen-nitrogen. In these diagrams taken from K. D. Timmerhaus and T. M. Flynn, *Cryogenic Process Engineering*, Plenum Press, 1989, pp. 296–297, the upper curve at a given pressure defines the dew point and the lower curve defines the bubble point. Looking at FIG. 4 for a pressure of 0.101 MPa, if there is a gas mixture with 10 mole percent nitrogen (point 1), condensation will start when the gas has cooled to the dew point curve (point 2g) which is at a temperature of about 89.5 K in this case. Because oxygen has a higher boiling point than nitrogen, the initial liquid formed (point 2f) will have only 7.4 mole percent nitrogen. If the temperature is lowered to point 3, the liquid will have the composition of point 3f while the remaining vapor will have the composition of point 3g. As the temperature is lowered further to point 4f or below, all of the mixture liquefies and the composition is 10 mole percent nitrogen, the same as at point 1. If this liquid is heated, the nitrogen which has a lower boiling point will vaporize first. Thus, the composition of the first vapor formed will be that of point 4g or about 30 mole percent. As the remaining liquid boils, the mole percent of nitrogen in the vapor drops back to 10 mole percent when point 2g is reached. It is believed that the composition swings with a ternary mixture of oxygen, argon and nitrogen will be even more pronounced than those shown in FIGS. 3 and 4 for binary mixtures. Fortunately, this concern was avoided when the system was set so that only 20 to 99% of the incoming flow to the condenser was actually condensed and when the condenser was controlled in accordance with the parameters as explained herein. This is believed to work because the excess flow operates to purge the vapor with higher impurity concentration from the system and avoid the aforementioned problem. Instead, the results realized were that a high concentration stream of oxygen could be liquefied and stored as set out in the portable ambulatory device claimed herein.

Figure 5:
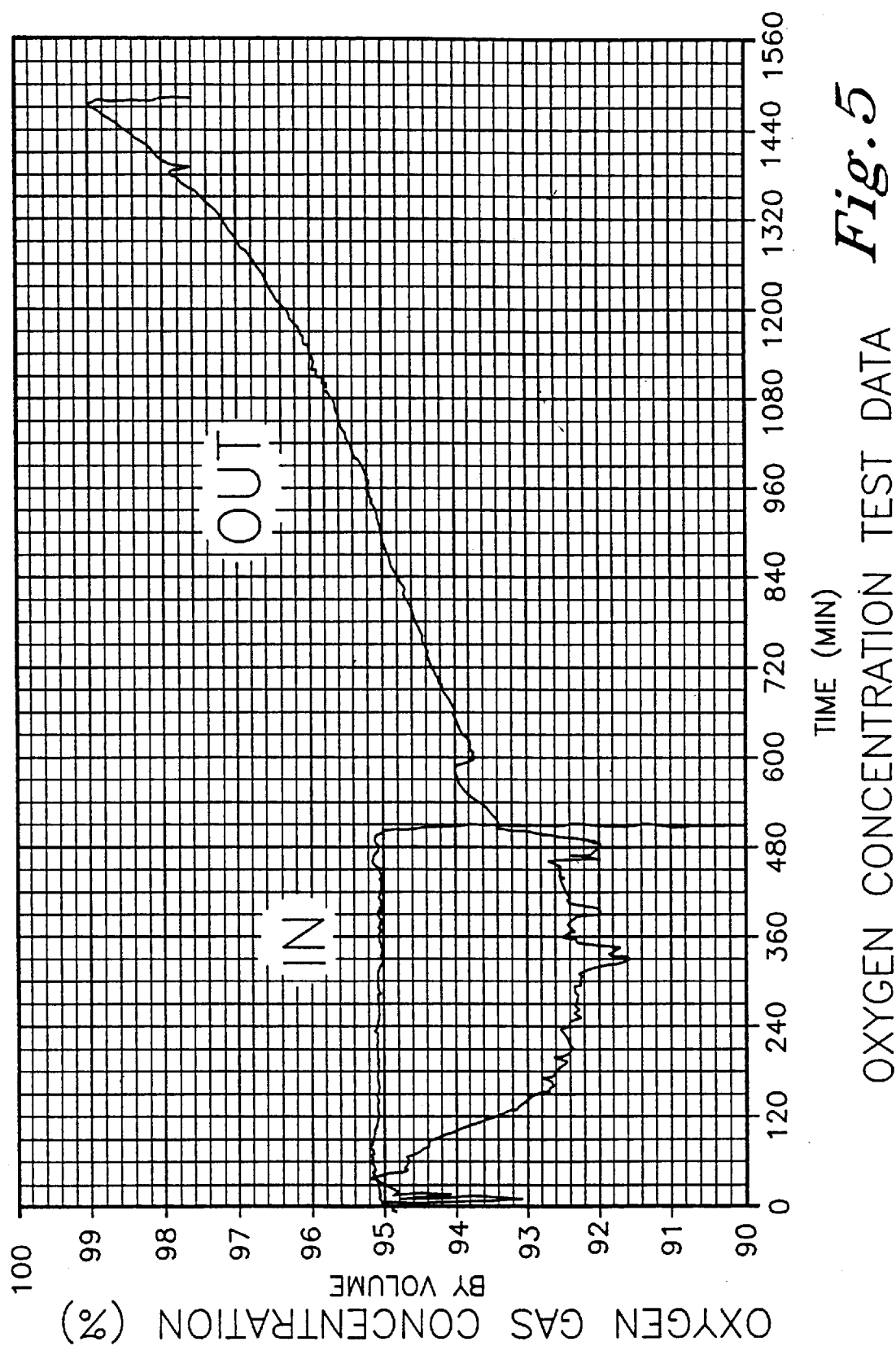
FIG. 5 shows typical oxygen concentration test data for gas streams into the condenser and out of the dewar during liquefaction, and out of the dewar as the liquid is re-vaporized. (Oxygen source is a PSA oxygen concentrator.)

FIG. 5 shows typical oxygen concentration test data for condensing and re-vaporizing part of the product outlet stream from the oxygen concentrator 11 in the preferred embodiment. For the first 120 minutes after the system was turned on, the system was cooling down without any net liquid accumulation in the dewar 14. From this point up to about 500 minutes, condensation continued with liquid accumulation. During this time phase, the inlet stream to the condenser 13 had an oxygen concentration of 95%, while the vent flow through line 52 had an oxygen concentration of only 92–93%. After 500 minutes the inlet stream and condenser cooling were stopped. The oxygen concentration of the re-vaporized liquid increased as the liquid boiled off due to the lower boiling point components (argon and nitrogen) boiling off first. This change in oxygen concentration presents no problem for medical ambulatory use because the oxygen concentration remains above 85%.

Because of the aforementioned mixture problem, it is important and even critical not to let the amount of argon and nitrogen in the liquid become too high or when it is revaporized, the oxygen concentration will initially be much lower than that conventionally used in supplemental oxygen therapy (>85%). This can be accomplished by selecting the proper condenser temperature, which is a function of pressure, and by not condensing all of the incoming flow. If only part of the incoming flow (20–99%) is liquefied, the remainder of the flow will purge the vapor with higher impurity concentration from the system. A condenser temperature of about 90 K (for ~17 psia) minimizes the amount of argon and nitrogen liquefied without overly diminishing the yield of oxygen. Hence there will be both liquid and vapor leaving the condenser. The liquid will fall into the dewar 14 and collect. The vapor which has not condensed is vented to the atmosphere through line 52 and the recuperator 15.

The amount of incoming flow liquefied is controlled by setting the mass flow rate relative to the cooling capacity of the cryocooler. The parameters of the condenser and/or cryocooler can be stored in the memory of the controller and/or computer and the controller regulating the incoming flow depending on the parameters stored and/or sensed. Having a mass flow rate which exceeds the cooling capacity of the cryocooler/condenser combination, prevents the incoming flow from being completely liquefied. The mass flow rate is controlled by the amount of flow restriction between inlet valve 19 and flow control valve 25. This includes the flow losses of the valves themselves as well as those in the recuperator, condenser, and all of the interconnecting plumbing.

The pressure in the dewar 14 is maintained slightly above ambient pressure while the cryocooler is operating by valve 25. It is desirable to keep the pressure in the condenser as high as possible because this increases the condensation temperature (as shown in FIGS. 3 and 4) which eases the requirements on the cryocooler. Once again this can be controlled by the controller and/or the computer, microprocessor and memory system.

This pressure regulating function of the solenoid on-off valve 25 is accomplished by the pressure transducer 9 and controller 16. Alternately, a back pressure regulating valve (such as a Tescom BB-3 series) or a suitable servomechanism may be used in lieu of the actively controlled solenoid. Liquid keeps accumulating in the dewar 14 until the liquid level sensor 17 signals the controller that the dewar is full or until the oxygen sensor 18 signals that the oxygen concentration of fluid exiting the oxygen concentrator 11 is too low.

In the best mode, operating parameters for optimal operation of the system for the condenser should be that the condenser surface temperature should be in the range from 69.2–109.7 K and pressure should be in the range from 5–65 psia. The gas concentrations into the condenser for medical use should have oxygen in the range of 80–100%, nitrogen from 0–20%, and argon from 0–7%.

In order to transfer liquid from the dewar 14; e.g. to fill a portable LOX dewar 23, the pressure in the dewar 14 must be increased so that liquid can be forced up the dip tube 20. As shown in FIG. 1, heater 21 is used for this purpose. Heater 21 may be immersed in the liquid oxygen or attached to the outer surface of the inner vessel. The controller 16 ensures that the cryocooler 12 is turned off and valve 25 is closed before the heater 21 is energized. The heater 21 remains turned on until the pressure, measured by pressure transducer 9, reaches about 22 psig.

Figure 22:
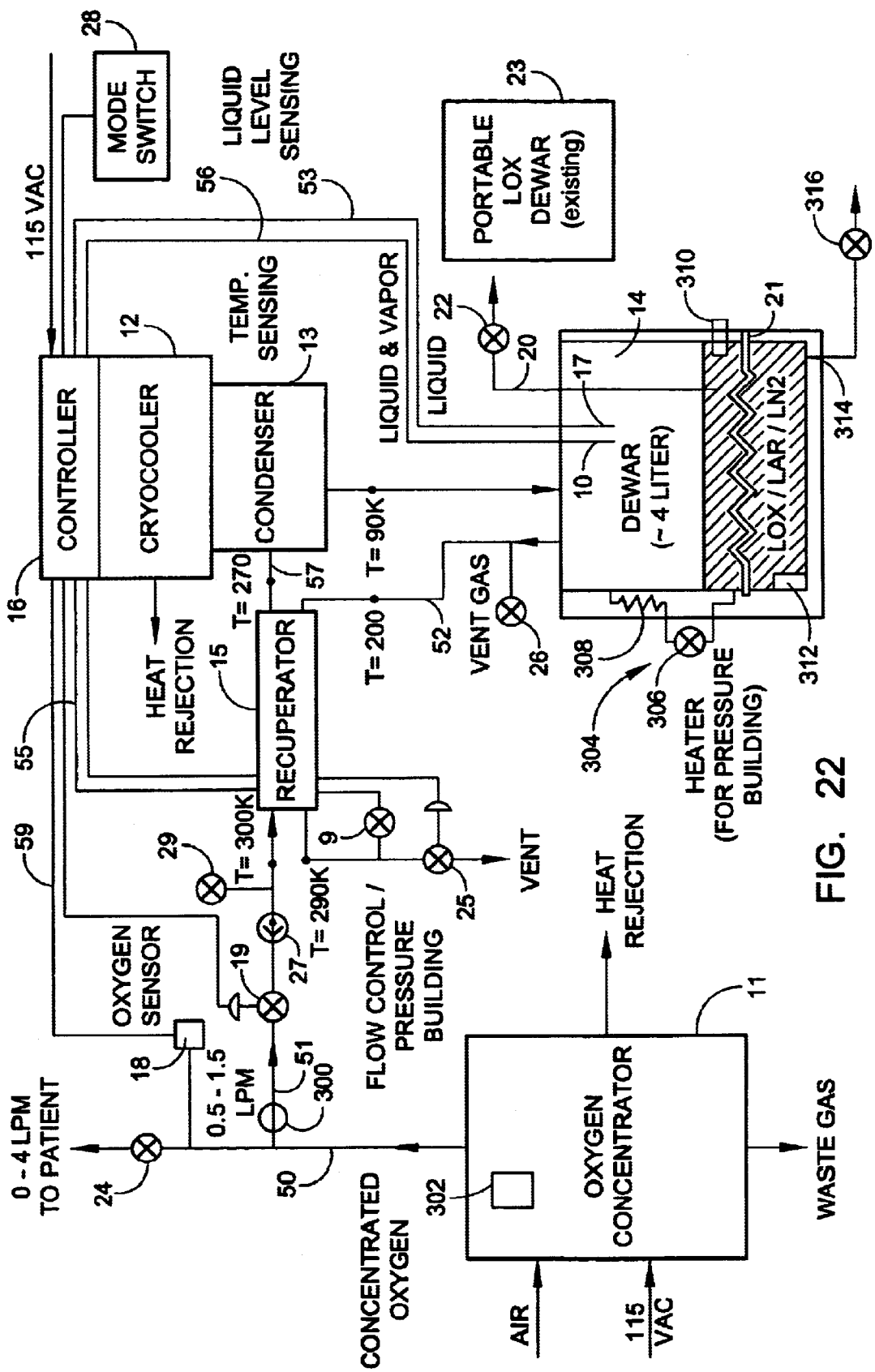
FIG. 22 is a block diagram of the invention in the medical oxygen preferred embodiment where gaseous oxygen is split off and liquefied for storage in a stationary dewar, similar to FIG. 1, and shows numerous means for transferring liquid oxygen from the storage dewar.

With reference to FIG. 22, other alternative means for transferring or dispensing liquid from the dewar 14 will now be described. For simplicity, the alternative liquid transferring means are described with respect to this one Figure. It will be readily apparent to those skilled in the art that any, any combination, or all of the disclosed liquid transferring means discussed below could be used in a single home liquid oxygen ambulatory system.

An alternative means for transferring liquid by raising the pressure in the dewar 14 includes adding a compressor 300 between the oxygen concentrator 11 and the condenser 13. The compressor 300 is preferably added in line 51, either before or after valve 19. The compressor 300 increases the pressure in the storage dewar 14 so that when the portable dewar 23 is engaged, liquid is forced up the dip tube 20 and into the portable dewar 23. An additional benefit of adding a compressor 300 at this location is that it increases the pressure during liquefication in the dewar 14, which increases the saturation temperature. An increased saturation temperature eases the cooling requirements on the cryocooler 12.

A further means for transferring liquid by raising the pressure in the dewar 14 includes using a high-pressure compressor 302 within the oxygen concentrator 11 instead of the typical low-pressure compressor. The high-pressure compressor 302 has the effect of increasing the pressure in the storage dewar 14 so that when the portable dewar 23 is engaged, liquid is forced up the dip tube 20. In addition to easing the cooling requirements on the cryocooler 12, a compressor 302 at this location slightly enhances the PSA cycle.

A still further means for transferring liquid by raising the pressure in the dewar 14 includes using a vaporizer loop 304. In this embodiment, the dewar 14 preferably remains at low pressure while liquid is being produced. When transfer of liquid out of the dewar 14 is desired, a valve 306 is opened to allow some liquid to flow into a coil 308 to be vaporized. This would increase the pressure in the dewar 14 so that liquid could be transferred to the portable dewar 23.

Another means for transferring liquid by raising the pressure in the dewar 14 includes a controllable heat leak such as a conductive strap 310 between ambient and the inner vessel of the dewar 14. When transfer of liquid out of the dewar 14 is desired, the heat leak is controlled so that heat from the ambient is transferred to the liquid, causing it to vaporize. This would increase the pressure in the dewar 14 so that liquid could be transferred to the portable dewar 23.

Another means for transferring liquid by raising the pressure in the dewar 14 includes a controllable pump 312 that is actuated when transfer of liquid out of the dewar 14 is desired.

An additional means for transferring liquid without raising the pressure in the dewar 14 includes incorporating a gravity-assisted dispensing mechanism 314 such as a controllable spigot (analogous to those used to dispense liquids from a large insulated cooler) near the bottom of the dewar 14. Unlike the alternative means for transferring liquid from the storage dewar 14 described above, which expel liquid out of the dip tube 20, the gravity-assisted dispensing mechanism eliminates the need for the dip tube 20. The gravity-assisted dispensing mechanism 314 preferably includes a quick disconnect valve 316 or other flow control means, similar to disconnect valve 22 described above, located on the end of the mechanism 314 to allow for connection of a portable dewar 23.

An additional means for transferring liquid without raising the pressure in the dewar 14 includes incorporating a portable dewar 23 adapted to be filled from a pressure less than 20 psig, which is the standard for currently available home stationary liquid dewars. For example, the portable dewar 23 may be adapted to be filled from a pressure such as 5 psig.

A further means for transferring liquid without raising the pressure in the dewar 14 involves replacing the storage dewar 14 with a specially designed portable dewar 23 such as that described above with respect to FIG. 2, which interfaces with the rest of the home liquid oxygen ambulatory system.

In order to eliminate accumulation of solid water and hydrocarbons which may be supplied in trace amounts from the oxygen concentrator, the dewar 14, recuperator 15, and condenser 13 will be warmed to room temperature periodically (preferably after about 30 fillings of a portable dewar, or every two months). This procedure is accomplished most economically when the inventory of liquid in the storage dewar is low; e.g. shortly after liquid transfer and a portable dewar has been filled. In this "boil-dry" mode, valve 19 will be closed, the cryocooler 12 is turned-off, valve 25 is open, and heater 21 is energized until all the liquid has boiled-off as evidenced by, for example, the temperature sensor 10 being above 125 K. The heater will boil-off the remaining liquid in the dewar 14 and with it any trace amounts of water and hydrocarbons which are condensed and solidified in the liquid oxygen or on the cold surfaces. Once valve 19 is re-opened, the flow of concentrated oxygen gas purges and removes most of the water vapor and hydrocarbons from the liquefier. The heater 21 will remain turned on until the dewar temperature, measured by temperature sensor 10, has warmed to about 300 K. Any remaining water vapor will be flushed out by gaseous oxygen during the subsequent cool-down.

The dewpoint/frostpoint of the gas stream provided by the oxygen concentrator is below −55° C. Although the mass of water flowing into the liquefier is quite small, the ice/frost formed at such a cold temperature has a very low density and hence, can take a appreciable volume of space that can lead to plugging of the liquefier. Therefore, the design of the recuperator 15 and/or condenser 13 must be able to allow for accumulation of frost without plugging.

Figure 19:
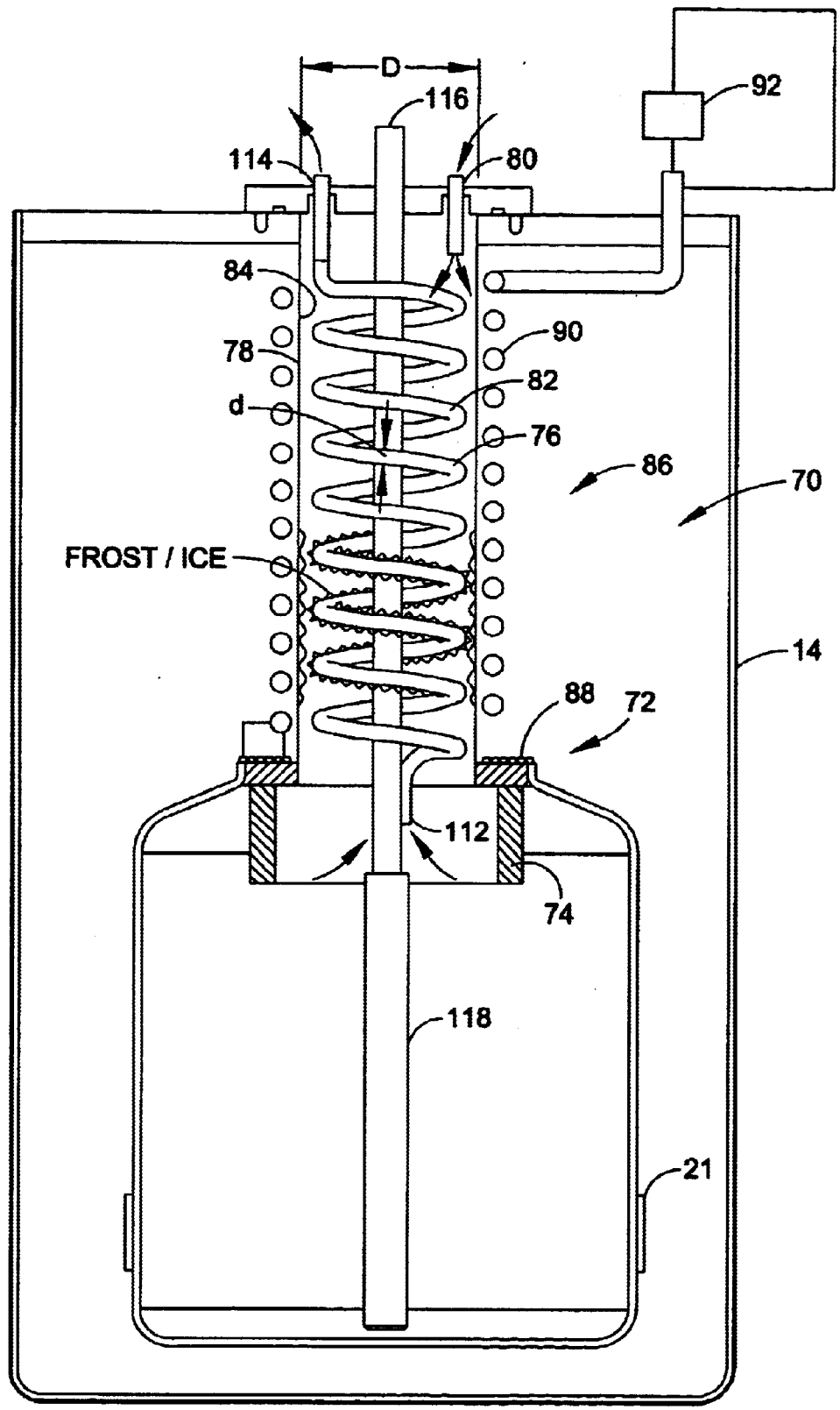
FIG. 19 is a cross-sectional view of an embodiment of a dewar having a liquefier with an integral vapor compression cycle coldhead, condenser, and recuperator, which is resistant to plugging and performance degradation caused by trace impurities in the gas stream such as water vapor, carbon dioxide and hydrocarbons.

With reference to FIG. 19, an embodiment of a liquefier 70, which is resistant to plugging, will now be described. Elements similar to those previously described are referred to with the reference numerals and are not described in further detail. The liquefier 70 includes an integral coldhead 72, condenser 74 and a recuperator 76 located generally within a dewar 14. Incoming gaseous flow enters a neck tube 78 via an inlet 80 as shown by the arrows. The gaseous flow includes mostly oxygen gas along with a small amount of water vapor and other trace impurities. The gaseous flow is pre-cooled as it passes the helical recuperator 76. Water vapor in the gaseous flow freezes out on surfaces at temperature below its frostpoint such as outer surface 82 of the recuperator 76 and inner surface 84 of the neck tube 78. The neck tube 78 has an inner diameter or dimension D and the helical recuperator 76 is constructed of a tube having an outer diameter or dimension d. By making inner diameter D of the neck tube 78 significantly larger than the outer diameter d of the helical recuperator tube 76 at locations along the neck tube 78 where incoming gaseous flow is present, the liquefier 70 allows for accumulation of frost on the inner surface 84 of the neck tube 78 or outer surface 82 of the recuperator 76 without plugging. This extends the period of time required between boil-dries without causing plugging in the liquefier 70.

Figure 20:
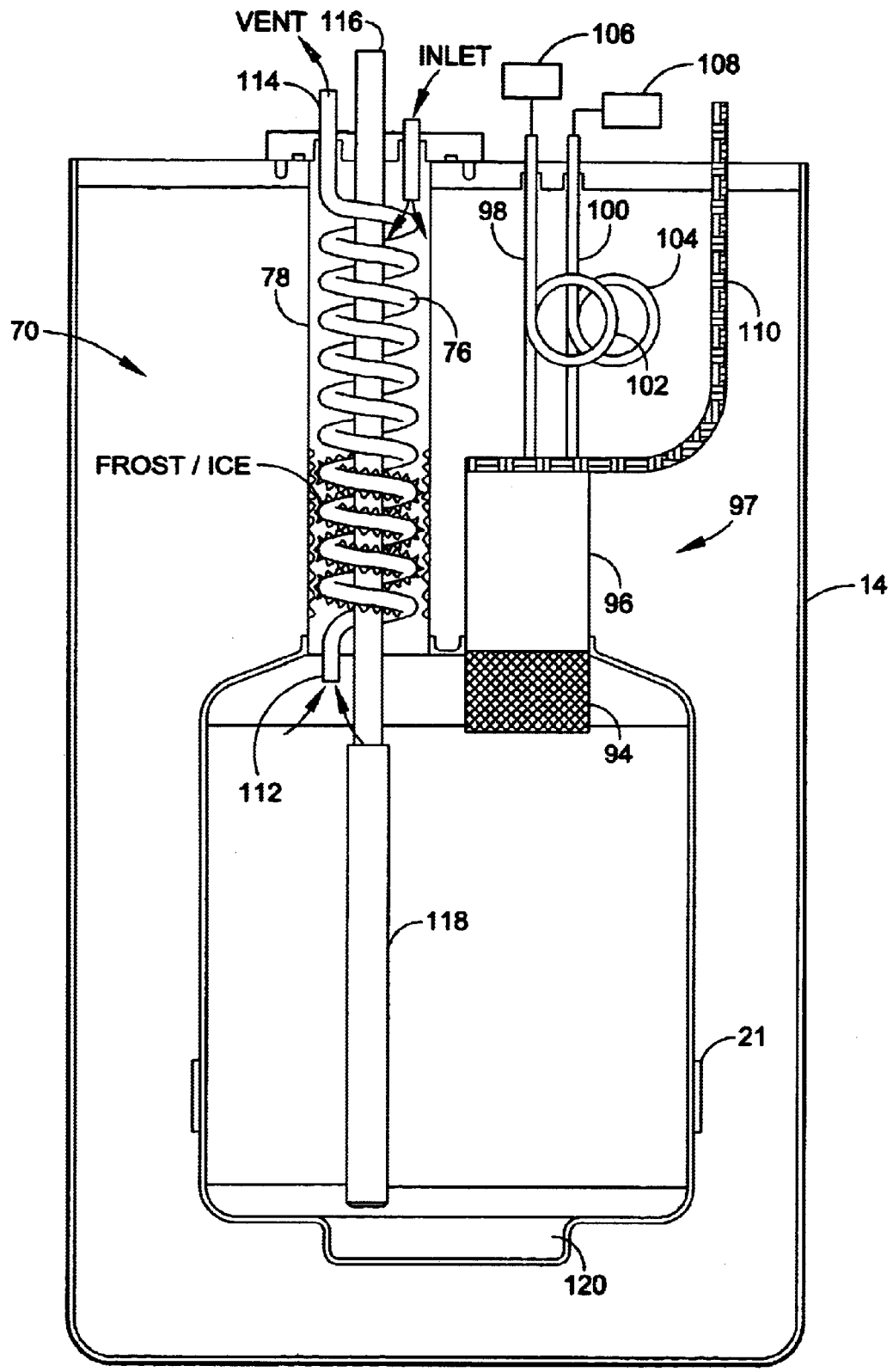
FIG. 20 is a cross-sectional view of an alternative embodiment of a dewar having a liquefier with an integral pulse tube or Sterling cycle coldhead, condenser, and recuperator, which is resistant to plugging and performance degradation caused by trace impurities in the gas stream such as water vapor, carbon dioxide and hydrocarbons.

Oxygen from the gaseous flow condenses into liquid oxygen at the condenser 74. The condenser 74 is shown in conjunction with a vapor compression cycle cryocooler 86 (evaporator 88, tube-in-tube heat exchanger 90, compressor 92) as its associated refrigerating mechanism. It will be readily understood by those skilled in the art that other refrigerating mechanisms may be used in conjunction with the condenser such as, but not by way of limitation, pulse tube, Stirling, etc. For example, with reference to FIG. 20, in an alternative embodiment of the invention, a condenser 94 may be used in conjunction with a coldhead 96 from a pulse tube cryocooler 97 to liquefy the incoming flow. The cryocooler 97 includes copper tubes 98, 100 that provide strain relief via respective coils 102, 104. Copper tube 98 connects the coldhead 96 to a compressor 106 and copper tube 100 connects the coldhead 96 to a reservoir volume 108. A flexible copper braid 110 provides a heat conduction path if needed to reject heat from the coldhead 96.

Excess gaseous flow not condensed becomes vent gas that is removed from the liquefier 70 via the recuperator 76. Vent gas enters the recuperator 76 through inlet 112, as shown by the arrows, flows through the helical recuperator 76 (providing the aforementioned pre-cooling) and preferably exits to the atmosphere through outlet 114.

The dewar 14 may include a central liquid withdrawal tube 116 for withdrawing liquid oxygen from the dewar 14. The central liquid withdrawal tube 116 may include an integral liquid level sensor 118 for monitoring the level of the liquid oxygen in the dewar 14. A heater 21 may be attached to the outer surface of the inner vessel of the dewar 14 to assist in transferring liquid oxygen from the dewar 14.

A getter cup 120 such as those used in commercial cryogenic dewars may be attached to the inner vessel of the dewar 14 to maintain a high vacuum in the dewar 14.

At initial start-up or after a periodic boil-dry phase, the dewar, condenser, recuperator, and all associated hardware are at room temperature and must be cooled down. This is accomplished in the "start-up" mode, where valve 19 (see FIG. 1) is open, the heater is off, the cryocooler is on, and valve 25 is modulated to control the pressure/flow rate. It is desired to keep the pressure and hence the density of the gas as high as possible while maintaining the flow rate.

The higher density gas will have better heat transfer with the dewar walls and associated hardware. It is noted that higher flow rates will enhance the convection heat transfer but may exceed the cooling capacity. Based on the cooling characteristics of the cryocooler between room temperature and 90 K, the flow rate can be changed to minimize the cool-down time.

The dewar 14 is equipped with at least one relief valve 26 as a safety feature. Another relief valve 29 is provided and in communication with the inlet gas stream 51, before flowing into the recuperator 15. This serves as a back-up for relief valve 26 as well as providing a means to eliminate accumulated water from the recuperator 15 during periods when the cryocooler 12 is off, if valve 25 is closed. A check valve 27 is also provided to prevent backflow into the oxygen concentrator in the event of a malfunction.

Figure 6:
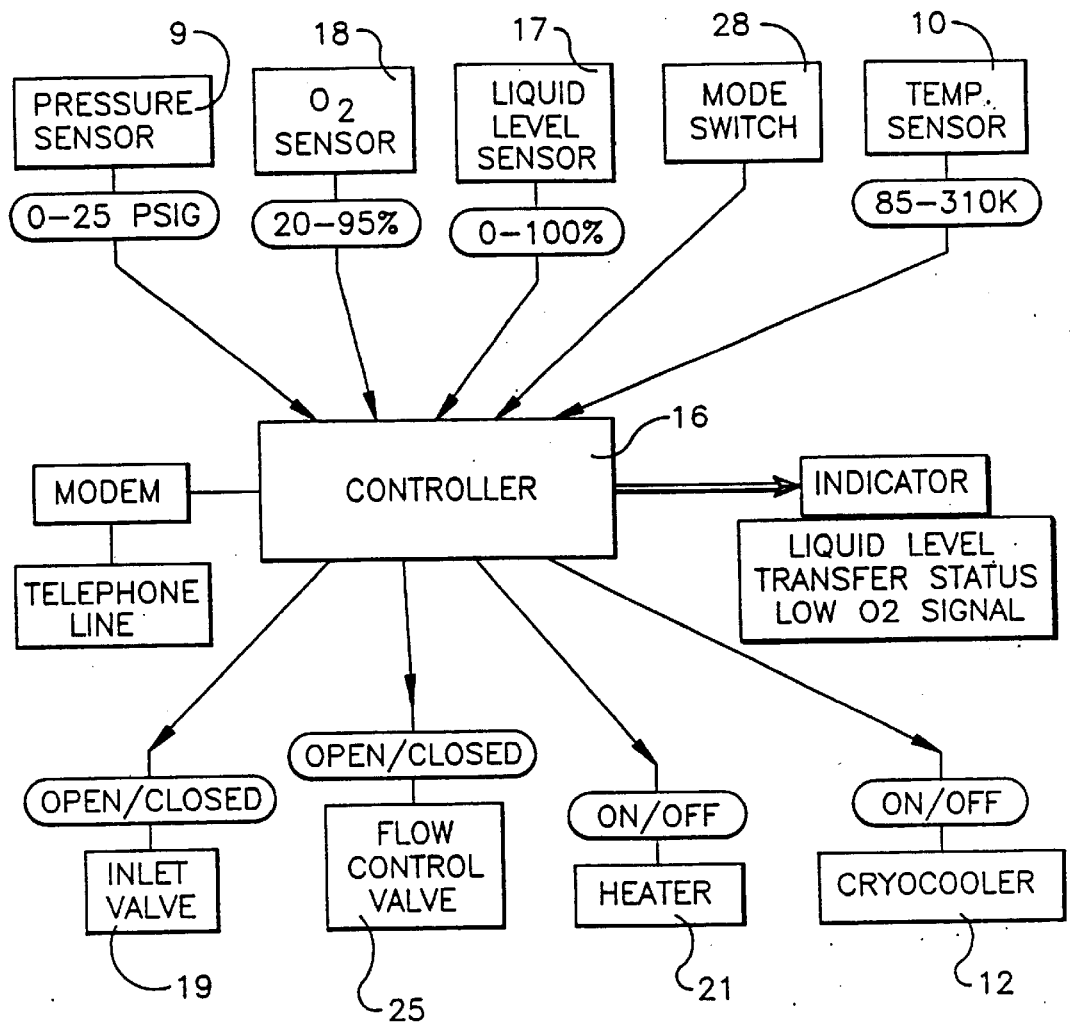
FIG. 6 shows the controller block diagram for operation of the system.
Figure 7A:
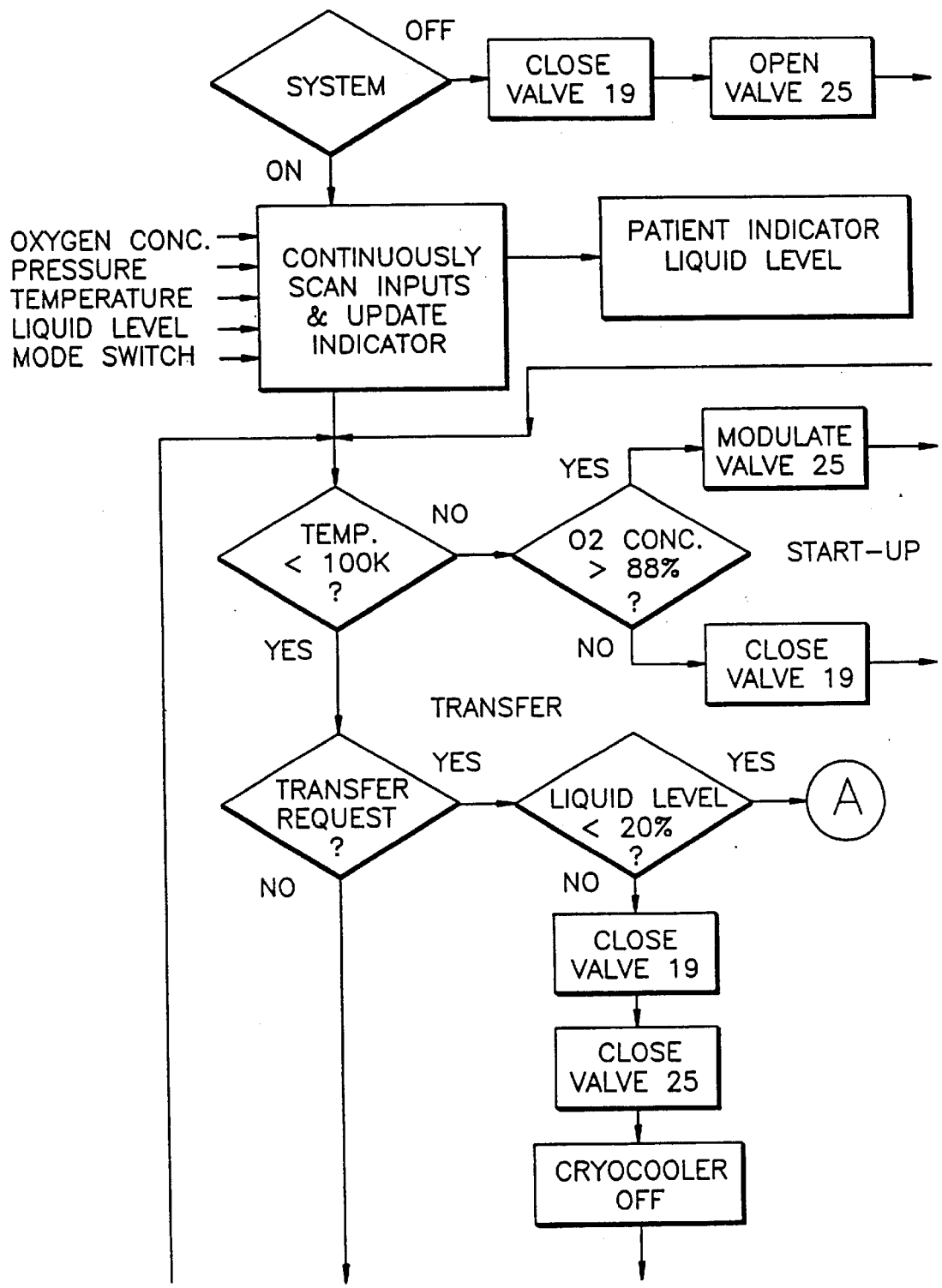
FIGS. 7A through 7D are flow charts showing the controller logic.
Figure 7B:
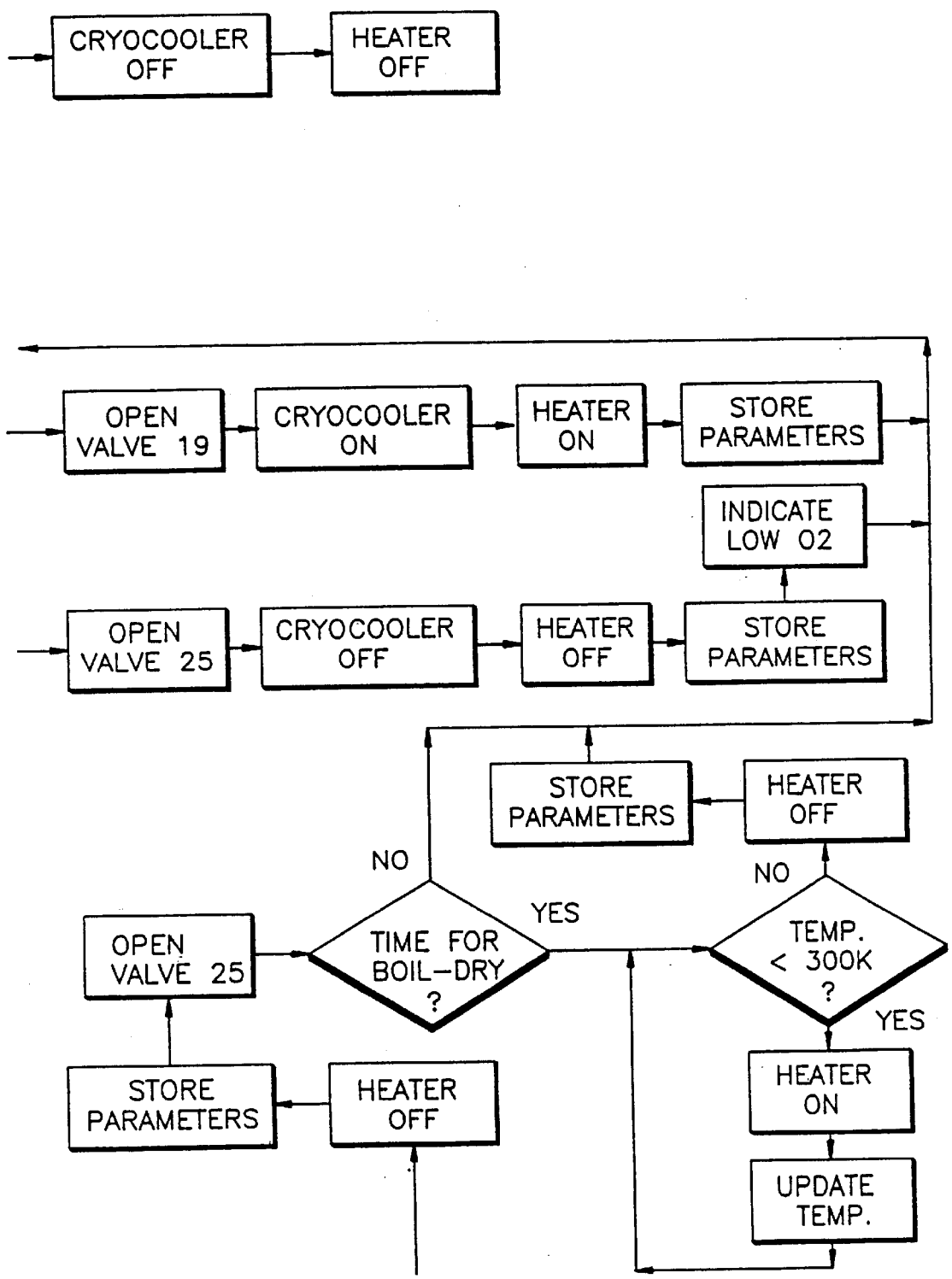
Figure 7C:
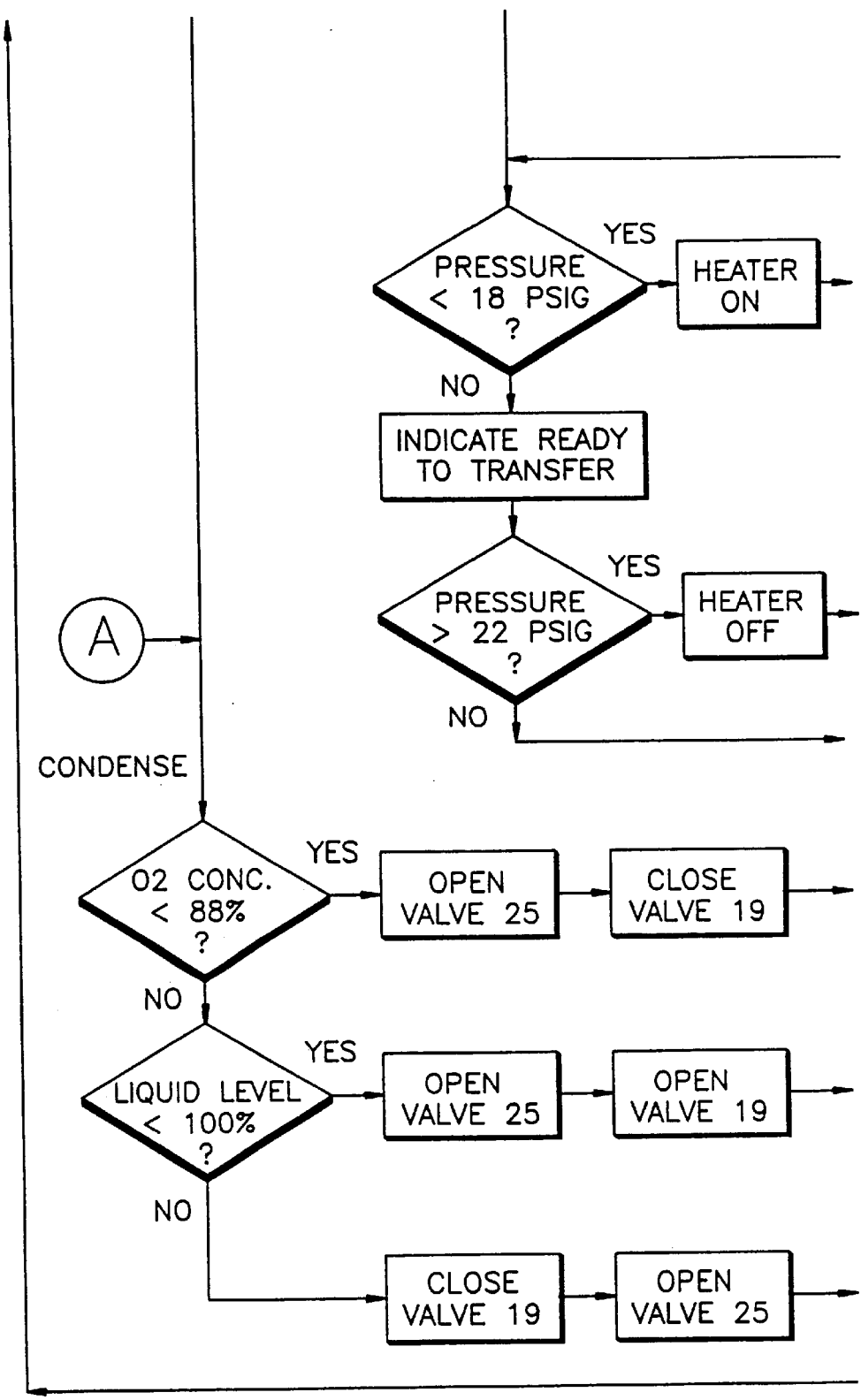
Figure 7D:
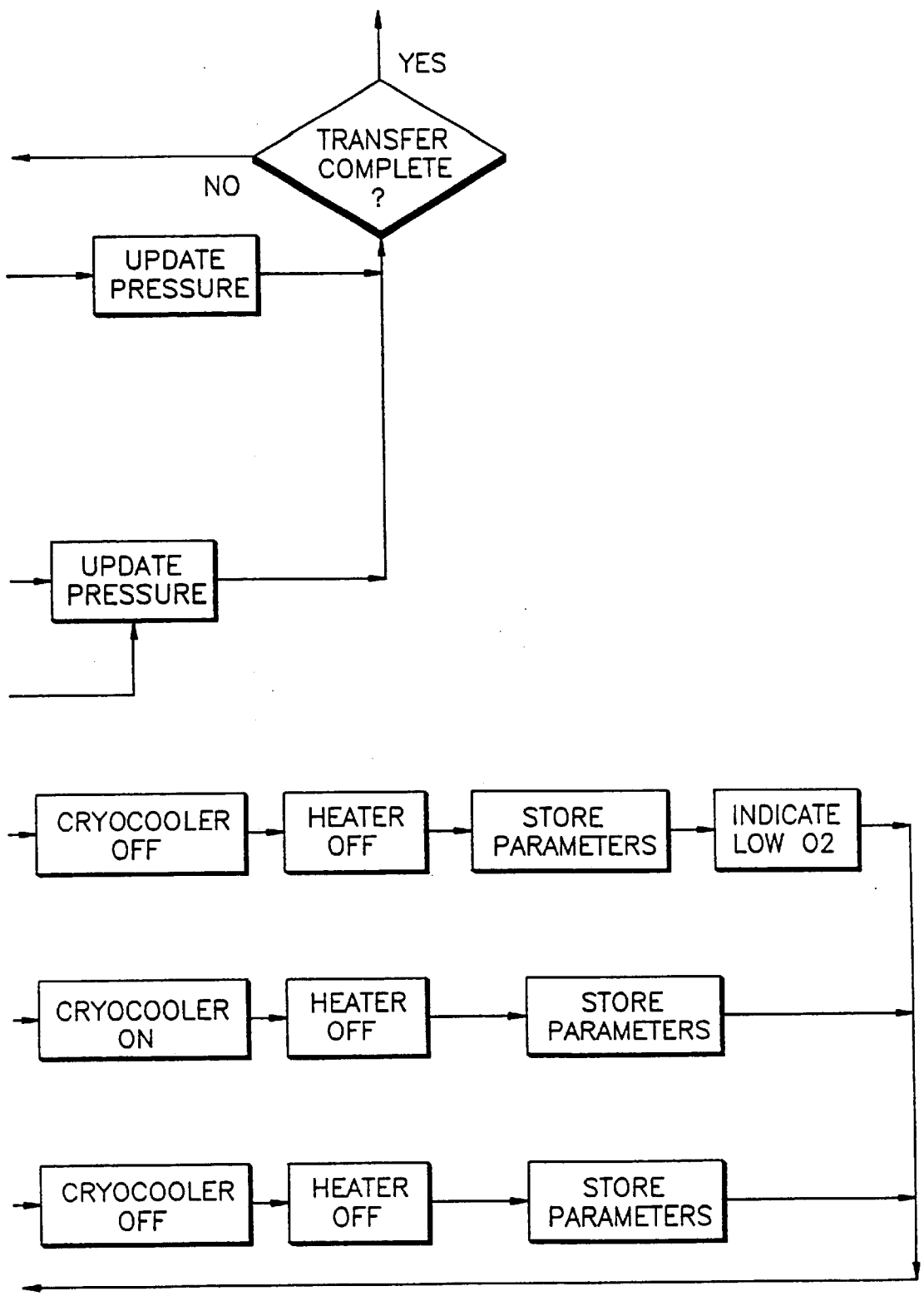

FIG. 6 provides a block diagram of the controller 16 control system with sensor input value ranges and output states. It also shows interfaces to an indicator and a modem or wireless interface. The mode switch 28 may be used by the patient to request the system to prepare for a liquid transfer to a portable dewar. The indicator then provides a visual signal that the system is building pressure in the dewar. Once the pressure has reached the desired value, a visual and/or audio signal is given to alert the patient that the system is ready to transfer liquid. The controller may also be programmed to perform an unattended liquid transfer. The modem, telephone line or wireless interface connections are optional hardware that may be added to the controller to enable remote monitoring of the system by the home care provider (e.g., to assist with maintenance and repair) or insurance companies or health providers/administrators (e.g., to assess if patients are using enough ambulatory oxygen to justify payments, etc.).

FIGS. 7A–D show a logic flow chart for the controller for the normal operation modes. This can also be referred to as the "input/output control schedule." The mode switch 28 can also be used by a repair or factory technician to put the controller in a calibration mode which serves as a method to check and reset the program. As shown in FIG. 6, the indicator provides liquid level readout, transfer request status, and low oxygen concentration information to the patient. All of the sensors are continuously scanned to provide the controller with the latest information. FIGS. 8 through 11 provide detailed output states as a function of input levels for the normal operating modes (start-up, condense, transfer, and boil-dry), which can be referred to as the "Optimal Liquefaction Operational Schedule."

For example, FIG. 8 relates to the start-up mode; i.e., when the system is first turned on or after the boil-dry cycle. As shown in FIGS. 6 through 8 and as depicted in FIG. 1, at start-up mode, the liquid sensor 17 shows zero liquid volume in the dewar and, when the oxygen sensor 18 shows an oxygen concentration greater than 88%, valve 19 is open, heater 21 is off, cryocooler 12 is on, and the indicator or the controller indicates a cool-down state. Valve 25 is modulated to control pressure.

Once the system attains a cool enough temperature, steady state or normal operational condense mode is used. As shown in FIG. 9, the input to the controller 16 is such that when the oxygen sensor indicates oxygen concentration being greater than 88% and when the other criteria in the left-hand column of FIG. 9 are achieved, the output states set out in the right portion of the chart are attained. For example, when the level of the dewar is sensed as being full, the liquid level sensor indicates a level of approximately 100%, causing closure of valves 19 and 25, keeping the heater off, turning the cryocooler off, and having the indicator signal that the dewar is full.

The transfer mode in FIG. 10 is the stage where one can fill the portable thermos bottles or dewars 23 from the main storage dewar 14. The top portion of FIG. 10, for example, shows controller readouts where, if the liquid sensor indicates a liquid level of less than 20%, then the conclusion is computed that there is not enough liquid to transfer into the portable dewar from the main dewar as shown. When the operator wants to increase the pressure in the storage dewar to force the liquid oxygen into the portable dewar, the heater is activated, and when the pressure sensor indicates that the pressure exceeds 22 psig, as shown on the last line in the left-hand column of FIG. 10, the heater 21 is then turned off and the controller readout or indicator shows that the transfer of liquid oxygen can be made to the portable dewar.

Finally, FIG. 11 indicates the boil-dry mode, with valve 25 open to allow the vapor to escape, and the various parameters relating thereto.

Figure 12:
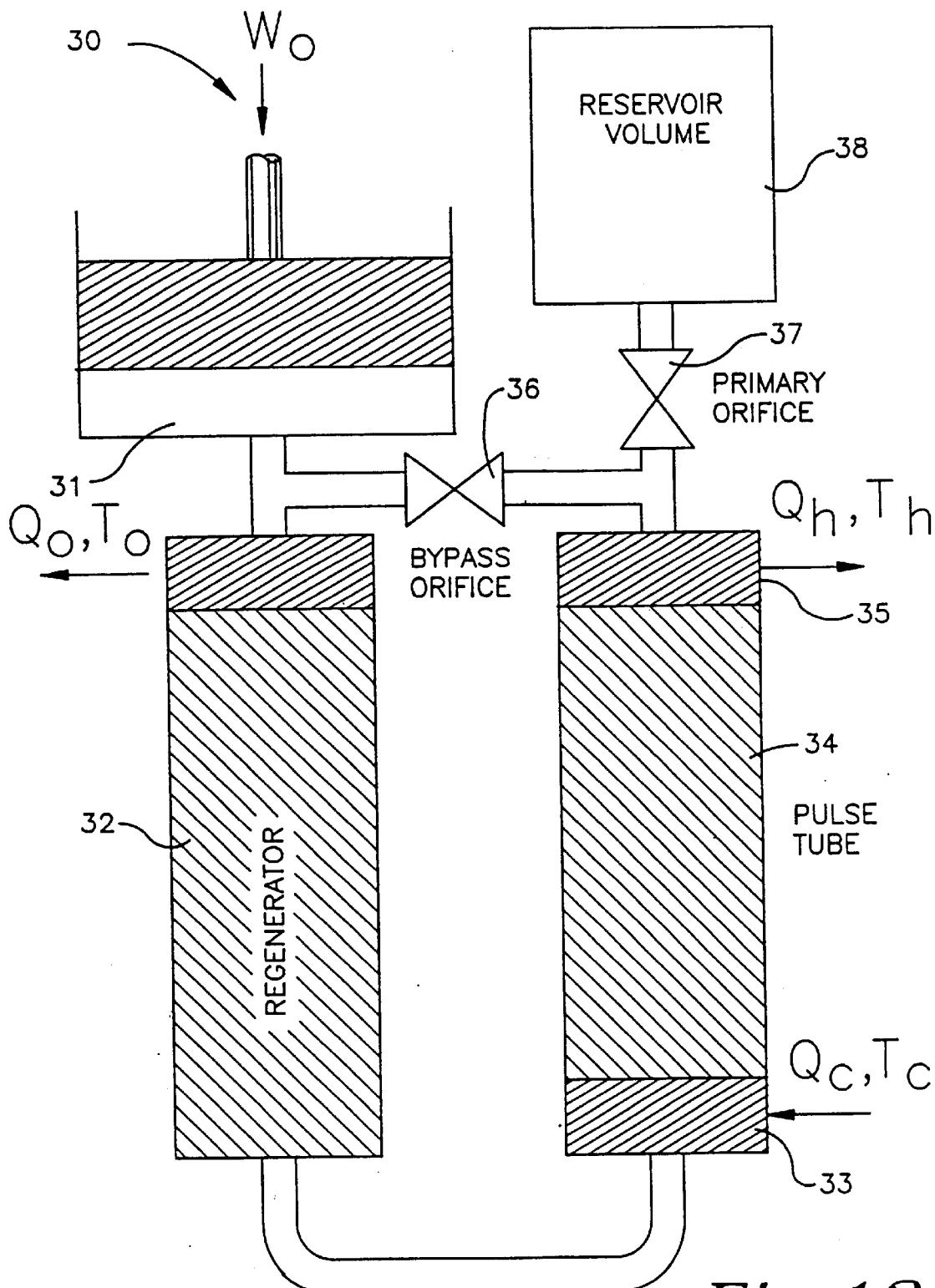
FIG. 12 illustrates basic components of a pulse tube refrigerator.

FIG. 12 shows a schematic of a pulse tube refrigerator, the preferred embodiment of the cryocooler 12 in FIG. 1. Because the cooling load on the condenser is small (7–15W), the pulse tube refrigerator is preferred for use in the subject ambulatory oxygen system because of its good efficiency with only one moving part, the pressure oscillator. Pulse tube refrigerators are shown in U.S. Pat. Nos. 5,488,830; 5,412,952 and 5,295,355 the disclosure of which are hereby incorporated by reference. FIG. 11 depicts a pulse tube refrigerator of the double inlet type. Other types of pulse tube refrigerators (PTR) could also be used such as the basic PTR or the inertance tube PTR (Zhu et al., $9^{th}$ International Cryocooler Conference, NH, June 1996).

The double inlet pulse tube refrigerator as shown in FIG. 12 is comprised of a pressure oscillator 30, primary heat rejecter 31, regenerator 32, heat acceptor 33, pulse tube 34, orifice rejecter 35, bypass orifice 36, primary orifice 37, and reservoir volume 38. The preferred refrigerant gas in the PTR closed and pressurized circuit is helium but various other gases such as neon or hydrogen could also be used. In operation, the PTR essentially pumps heat accepted at low temperature in the heat acceptor 33 to the orifice heat rejecter 35 where it is rejected at near ambient temperature. Although FIG. 12 depicts a "U-tube" configuration of the PTR, in-line and coaxial configurations are other possible options. Depicted therein is a piston type pressure oscillator, but other types are possible such as those utilizing diaphragms or bellows.

Figure 13:
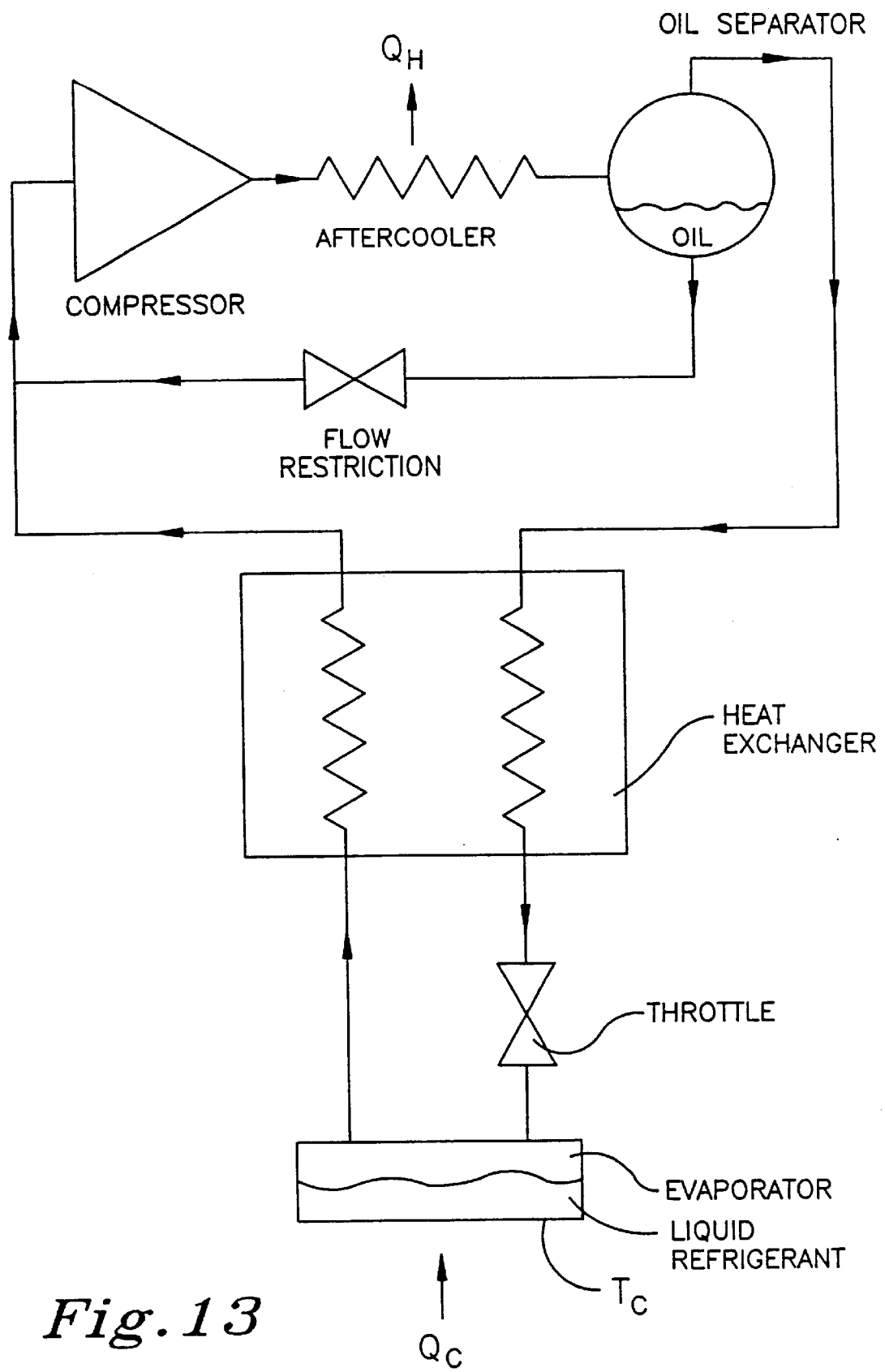
FIG. 13 illustrates another embodiment of a cryocooler which may be used in the subject invention.

FIG. 13 shows a schematic of another embodiment of the cryocooler. This is a vapor compression cycle cryocooler using a mixed gas refrigerant such as shown in U.S. Pat. No. 5,579,654; a 1969 German Patent by Fuderer & Andrija; British Patent No. 1,336,892. Other types of cryocoolers will work as long as they meet the important criteria of small size, convenience and low cost. In FIG. 13, the refrigerant is compressed by the compressor to high pressure. Then it is cooled by the aftercooler with heat Qh being rejected to the environment. Oil is separated in the oil separator. Oil flows back to the compressor inlet through a flow restriction. The refrigerant gas flows to a heat exchanger where it is cooled by the returning cold stream. Some components of the mixture may condense in this process. The liquid/gas refrigerant mixture flows through a throttle valve where its pressure is reduced and its temperature drops. This cold refrigerant enters the evaporator where the heat load Qc is absorbed and some liquid is boiled into vapor. This vapor flows up the cold side of the heat exchanger absorbing heat from the incoming stream. Then it flows back to the compressor. Heat Qc is accepted at cold temperature Tc. This is where the condenser would interface with the cryocooler.

It is noted that with this type of cryocooler, it may be possible to remove some of the heat from the oxygen stream at a temperature warmer than Tc.

Figure 14:
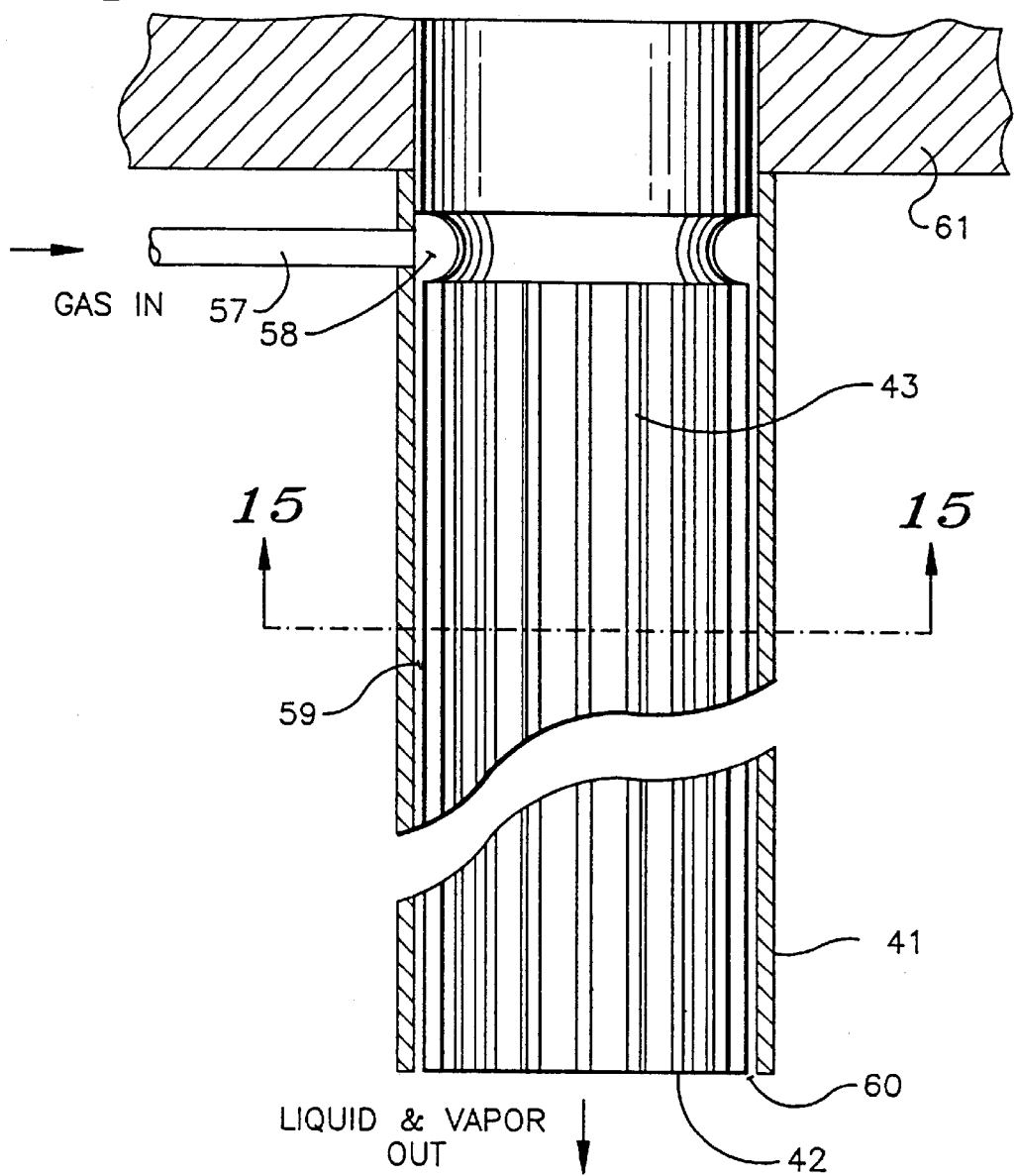
FIG. 14 is a side cross-sectional view of the preferred embodiment of the condenser.
Figure 15:
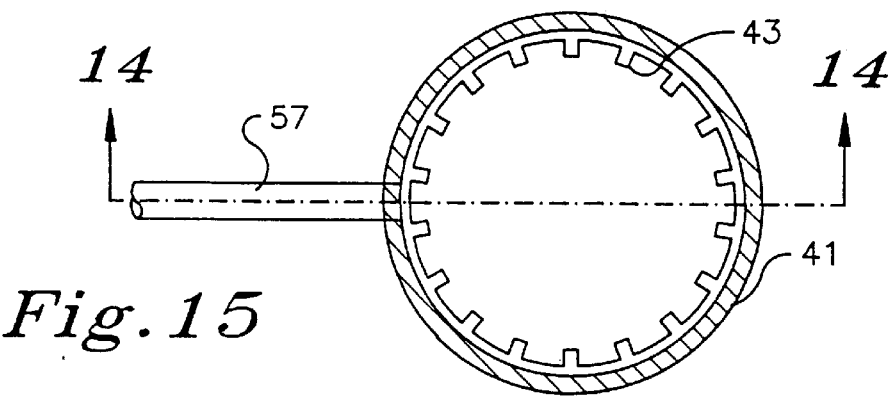
FIG. 15 is an end cross-sectional view of the preferred embodiment of the condenser corresponding to FIG. 14.

One possible geometry of the generally vertically oriented, gravity assisted condenser 13 in FIG. 1 is shown in FIGS. 14 and 15. The incoming gas from the oxygen concentrator flows from conduit 57 to chamber 58 and then is distributed through an annular passage 59 between the outer tube 41 and inner rod 42. The inner rod 42 is made of a high thermal conductivity material such as OFHC (Oxygen Free High Conductivity) copper, to minimize the temperature gradient between the surface on which the oxygen condenses (13) and the cryocooler 12. The cold end of the cryocooler is shown by cross-hatched member 61. Due to surface tension, the axial slots or grooves 43 will draw in liquid as it condenses. This will enhance heat transfer from the incoming gas by preventing a liquid film from forming over the entire condenser surface. Condensed liquid will drip off the bottom of the rod 42 while non-condensed gases flow out the end of the annulus 60. It is possible to liquefy all of the incoming flow to the condenser provided the cryocooler has sufficient cooling capacity and temperature capability. However, in order to minimize the amount of nitrogen and argon condensed, the preferred embodiment only condenses between 20–99% of the incoming flow. The incoming flow rate can be determined by the appropriate sizing of flow restrictions downstream of and by controlling valve 19. As mentioned previously, the mass flow rate is chosen to exceed the cooling capacity of the condenser/cryocooler so that only part of the incoming flow is liquefied. Also, the pressure in the condenser is maintained as high as possible while maintaining the desired flow rate. The higher pressure increases the condensation temperature which in turn reduces the requirements on the cryocooler.

Figure 16:
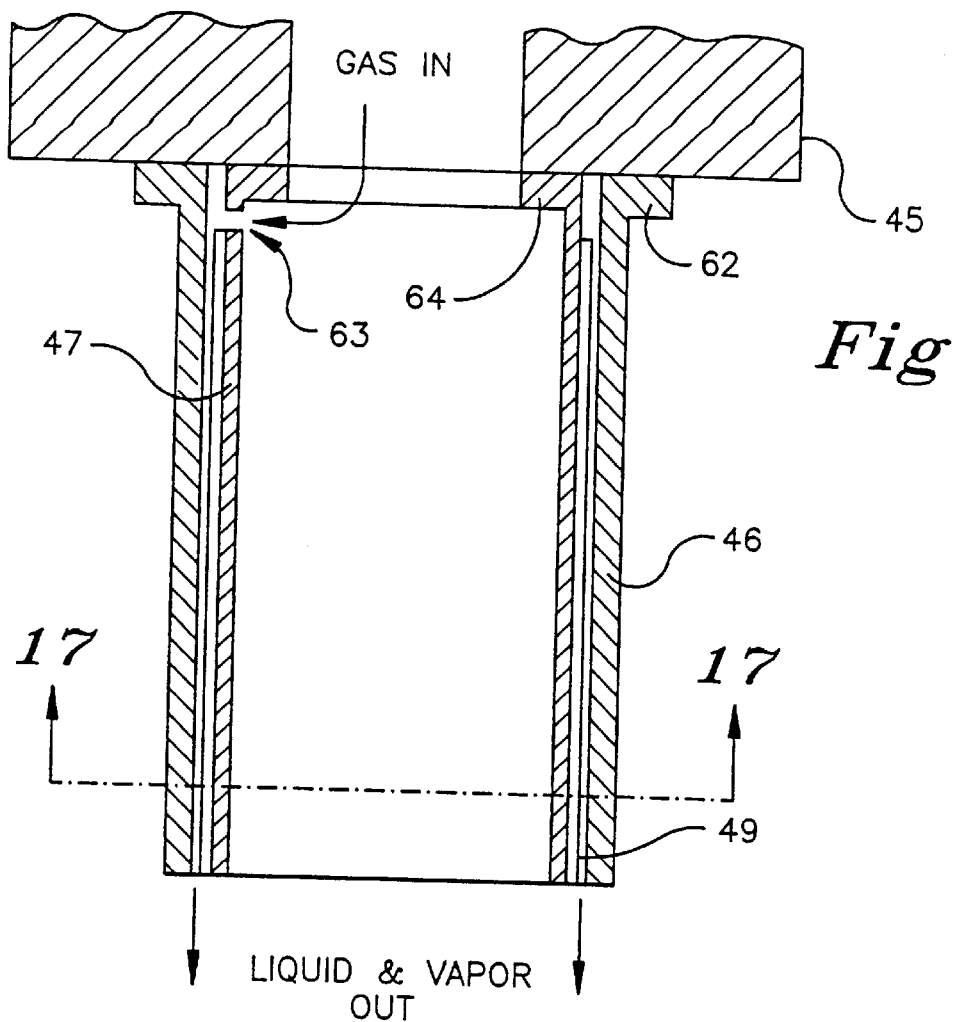
FIG. 16 shows a side cross-sectional view of another preferred embodiment of the condenser.
Figure 17:
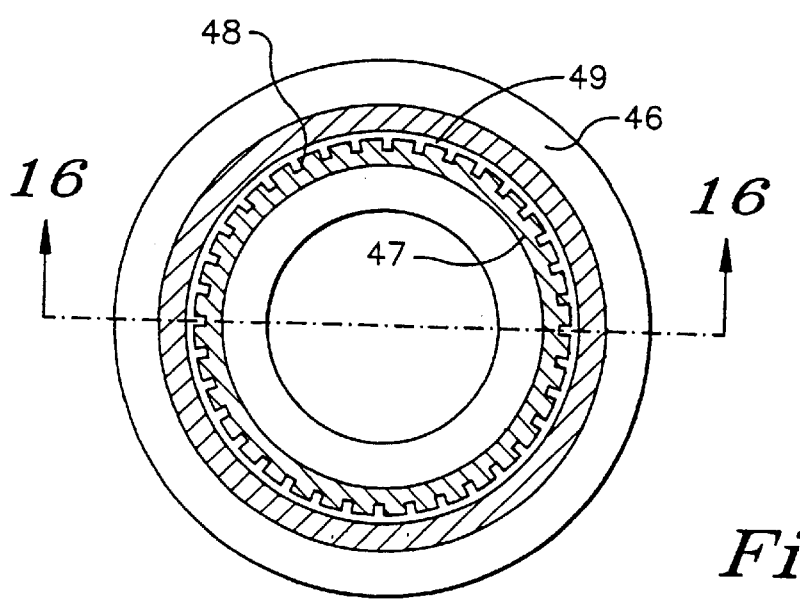
FIG. 17 shows an end cross-sectional view of another preferred embodiment of the condenser corresponding to FIG. 16.
Figure 18:
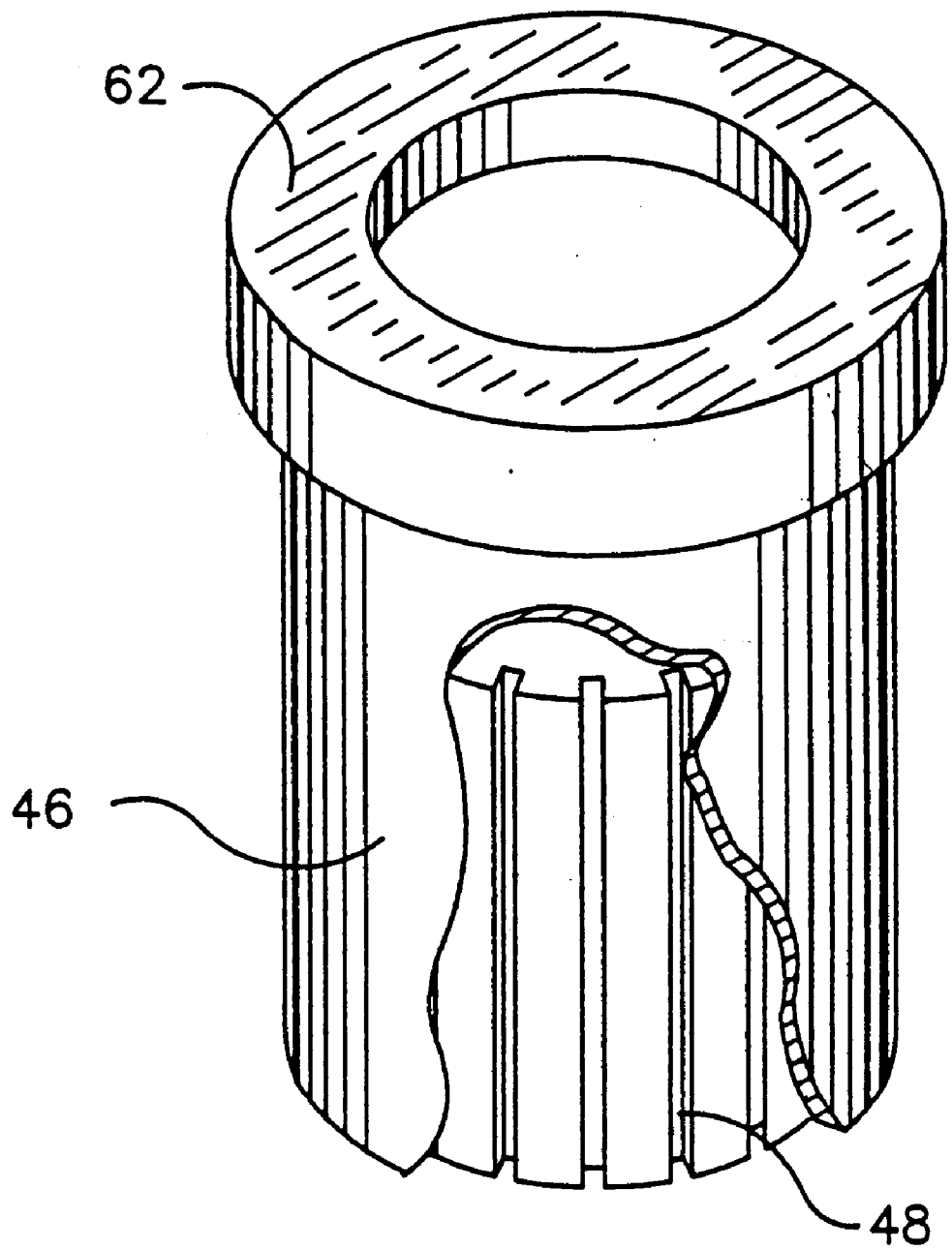
FIG. 18 is an isometric view of the embodiment of the condenser shown in FIGS. 16 and 17.

FIGS. 16 and 17 show another embodiment of the condenser that allows easier integration with the mixed gas refrigerant cryocooler. This configuration also allows access to the liquid in the dewar through the center of the condenser. The cold end of the cryocooler 45 is in thermal contact with an outer tube 46 and an inner tube 47, both of which are made of a high thermal conductivity material such as OFHC copper and which utilize flanges 62 and 64 to interface with the cryocooler. The inner tube has axial slots or grooves 48 cut into its outer surface (see, FIG. 17) to increase the surface area and to wick condensed liquid, preventing a liquid film from forming over its entire surface. Gas enters the condenser through port 63. The liquid and vapor flow down through an annular passage 49. An isometric view of this embodiment is shown in FIG. 18.

Figure 21:
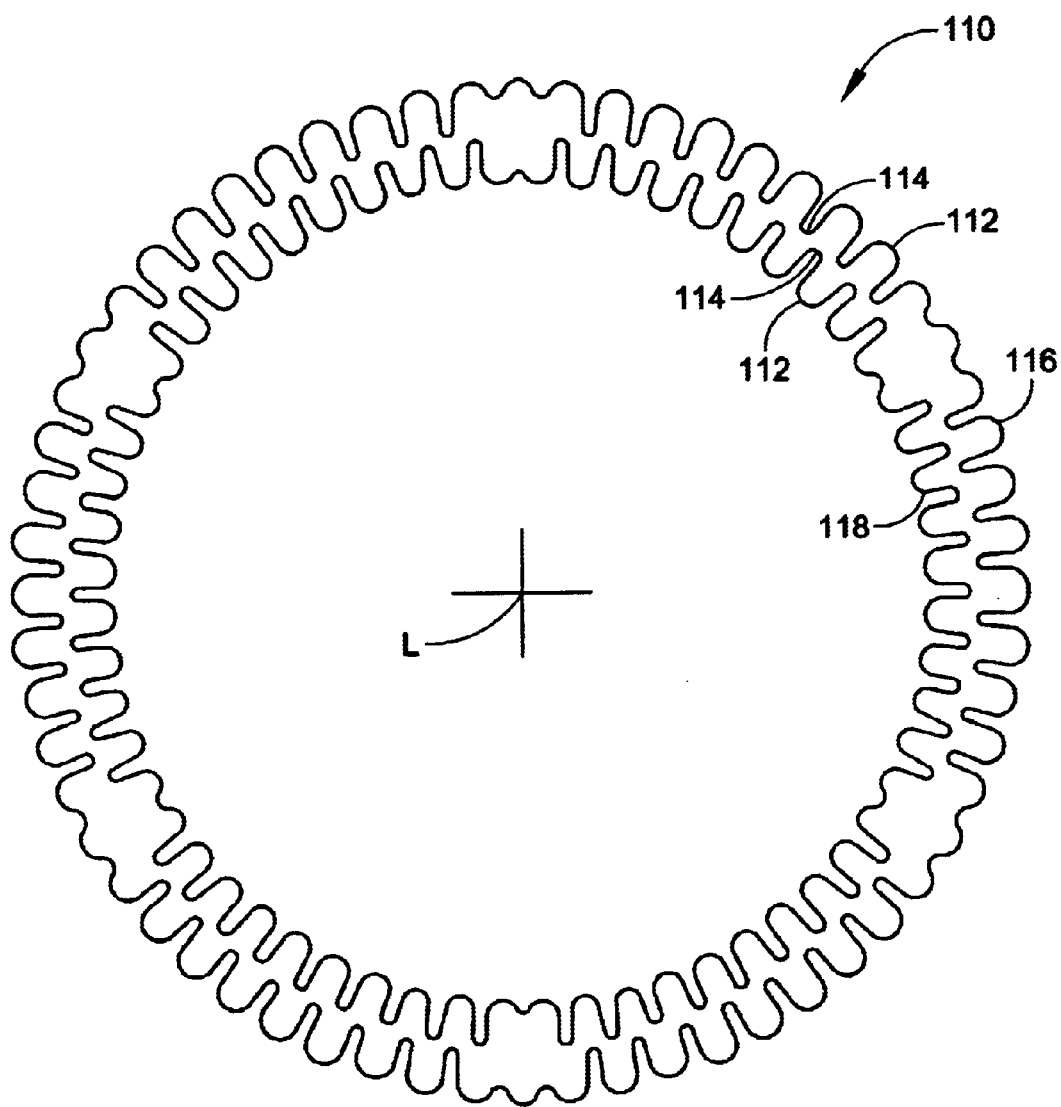
FIG. 21 is an end cross-sectional view, similar to FIG. 17, of an embodiment of a condenser having shaped fins to reduce the liquid film thickness.

FIG. 21 is a cross-sectional view, similar to the views in FIGS. 15 and 17, of another embodiment of a generally vertically oriented gravity assisted condenser 110. The condenser 110 includes fins 112 and corresponding flutes 114 that extend vertically the longitudinal length of the condenser 110 on both an exterior side 116 and an interior side 118 of the condenser 110, generally parallel with a vertical longitudinal axis L of the condenser 110. The vertical longitudinally elongated fins 112 and flutes 114 enhance condensation by using surface tension forces to maintain a small liquid film thickness on the condensation surface. A small liquid film thickness, $\delta$, allows for better condensation performance because the heat transfer coefficient (h) is equal to $k/\delta$ ($h=k/\delta$). The fins 112 preferably have a convex surface with a hyperbolic cosine profile to provide a uniform liquid film thickness and maximize condensation; however, other simpler convex curved surfaces that are more easily manufactured can be used with only slightly less performance. A convex surface for the fins 112 produces a small liquid film thickness and a concave surface for the flute 114 supports or receives a larger liquid film thickness. Thus, the convex surfaces of the fins 112 can be drained by concave surfaces of the flutes 114. Thus, the flutes 114 serve as drainage channels to keep the condensate from flooding the condensation surfaces. By making a condenser 110 with both vertical longitudinally elongated convex and concave portions, the overall condensation rates can be increased many fold even though the surface area is only increased a little.

In an alternative embodiment of the invention, the flutes 114 may have a profile that is other than convex such as, but not by way of limitation, generally rectilinear or generally V-shaped.

In a further embodiment of the invention, the fins 112 and flutes 114 may exist on only the exterior side 116 or interior side 118 of the condenser 110. Alternatively, the condenser 110 may have fins 112 and flutes 114 on the interior and/or the exterior and the condenser 110 is used in conjunction with another condensing device such as another condenser located within the interior 118 and/or around the exterior 116 of the condenser 110.

Prior art (U.S. Pat. Nos. 4,253,519, 4,216,819) has been limited to horizontal externally fluted tubes with purely radial conduction through the tube wall. In contrast, the condenser 110 of the present invention may include fins 112 and flutes 114 on both sides 116, 118. Also, heat is conducted axially in the condenser 110 of the present invention.

Thus, an improved home/ambulatory liquid oxygen system is disclosed. While the embodiments and applications of this invention have been shown and described, and while the best mode contemplated at the present time by the inventors has been described, it should be apparent to those skilled in the art that many more modifications are possible, including with regard to scaled-up industrial applications, without departing from the inventive concepts therein. Both product and process claims have been included and in the process claims it is understood that the sequence of some of the claims can vary and still be within the scope of this invention. The invention therefore can be expanded, and is not to be restricted except as defined in the appended claims and reasonable equivalence departing therefrom.

What is claimed is:

1. A home liquid oxygen ambulatory system for supplying a portable supply of oxygen, where a portion of the gaseous oxygen output obtained from an oxygen concentrator is condensed into liquid oxygen, comprising:
   (a) an oxygen concentrator which separates oxygen gas from the ambient air;
   (b) a condenser in communication with said oxygen concentrator for receiving and liquefying the oxygen gas flow;
   (c) a cryocooler associated with said condenser; and
   (d) a first storage dewar in fluid communication with said condenser and adapted to store the oxygen liquefied by the condenser, the first storage dewar including means for transferring liquid oxygen from the first dewar to a second dewar for storing a quantity of oxygen suitable for moveable oxygen treatment, wherein said liquid oxygen transferring means is adapted to increase the pressure in said first dewar.

2. The system of claim 1, wherein said liquid transferring means includes a heater immersed within the liquid oxygen in said first dewar.

3. The system of claim 1, wherein said first dewar includes an inner vessel in which said liquid oxygen reside, and liquid transferring means includes a heater attached to the outer surface of inner vessel.

4. The system of claim 1, wherein said condenser is in communication with said concentrator through a line, and said liquid transferring means includes a compressor located in said line between said condenser and said concentrator.

5. The system of claim 1, wherein said liquid transferring means includes a high-pressure compressor in communication with said concentrator for delivering high-pressure air thereto.

6. The system of claim 1, wherein said liquid transferring means includes a vaporizer loop associated with said first dewar.

7. The system of claim 1, wherein said liquid transferring means includes a controllable heat leak associated with said first dewar.

8. The system of claim 1, wherein said liquid transferring means includes a gravity-assisted dispensing mechanism.

9. The system of claim 1, wherein said system further includes said second storage dewar and said second storage dewar is adapted to be filled at a pressure below 20 psig.

10. A method for generating liquid oxygen in a home from a home liquid oxygen ambulatory system having an oxygen concentrator, a condenser, and cryocooler, a storage dewar and means for transferring liquid oxygen from the first dewar to a second dewar, comprising:

(a) generating a gaseous supply of oxygen using the oxygen concentrator;

(b) splitting off at least a portion of the gaseous supply to be liquefied;

(c) cooling said supply of oxygen using the condenser and cryocooler to transform the gaseous oxygen to liquid oxygen;

(d) storing the liquid oxygen in the storage dewar;

(e) transferring the liquid oxygen in the storage dewar with the liquid oxygen transferring means to a second dewar by increasing the pressure in said first dewar for storing a quantity of liquid oxygen from which smaller quantities can he transferred for moveable oxygen treatment.

11. The method of claim 10, wherein said liquid transferring means includes a heater immersed within the liquid oxygen in said first dewar and transferring the liquid oxygen includes heating the liquid oxygen in said first dewar so that the pressure is increased in said first dewar.

12. The method of claim 10, wherein said first dewar includes an inner vessel in which said liquid oxygen reside, said liquid transferring means includes a heater attached to the outer surface of inner vessel, and transferring the liquid oxygen includes heating the liquid oxygen in said first dewar so that the pressure is increased in said first dewar.

13. The method of claim 10, wherein said condenser is in communication with said concentrator through a line, and said liquid transferring means includes a compressor located in said line between said condenser and said concentrator, and transferring the liquid oxygen includes increasing the pressure of gaseous oxygen entering said condenser and said dewar with said compressor.

14. The method of claim 10, wherein said liquid transferring means includes a high-pressure compressor in communication with said concentrator for delivering high-pressure air thereto, and transferring the liquid oxygen includes increasing the pressure of gaseous oxygen entering said condenser and said dewar with said compressor.

15. The method of claim 10, wherein said liquid transferring means includes a vaporizer loop associated with said first dewar, and transferring the liquid oxygen includes heating the liquid oxygen in said first dewar with said vaporizer loop so that the pressure is increased in said first dewar.

16. The method of claim 10, wherein said liquid transferring means includes a controllable heat leak associated with said first dewar, and transferring the liquid oxygen includes heating the liquid oxygen in said first dewar so that the pressure is increased in said first dewar.

17. The method of claim 10, wherein said liquid transferring means includes a gravity-assisted dispensing mechanism.

18. The method of claim 10, wherein said system further includes said second storage dewar, said second storage dewar is adapted to filled at a pressure below 20 psig.

19. A liquefier for a home liquid oxygen ambulatory system that is resistant to plugging, the home liquid oxygen ambulatory system having an oxygen concentrator for delivering gaseous flow to the liquefier and a storage dewar having an inner vessel for storing liquid oxygen produced by the liquefier, comprising:

a condenser;

a refrigerating mechanism associated with said condenser;

means for communicating incoming gaseous flow from the oxygen concentrator to the condenser, said communicating means having an inner surface with a dimension D;

means for venting gaseous flow not condensed from the inner vessel, said venting means having an outer surface with a dimension d and disposed within said communicating means; and whereby the dimension D of the inner surface of the communicating means is significantly larger than the dimension d of the outer surface of the venting means to allow for the build-up of solid contaminants on the outer surface of the venting means without plugging up the communicating means.

20. The liquefier of claim 19, wherein said venting means includes a recuperator comprised of a helical coil of tubing, the tubing having said outer surface with a diameter of said dimension d, whereby the incoming gas stream flows over the outer surface of said helical coil of tubing and a vent stream flows inside said helical coil of tubing.

21. The liquefier of claim 20, wherein said outer surface of said helical coil of tubing has a cold surface to freeze out trace impurities of solid contaminants such as $H_2O$, $CO_2$ and hydrocarbons.

22. The liquefier of claim 19, wherein said communicating means is comprised of a neck tube having said inner surface with a diameter of said dimension D.

23. The liquefier of claim 19, wherein refrigerating mechanism is integral with the condenser.

24. The liquefier of claim 19, wherein the refrigerating mechanism and condenser are integral with said storage dewar.

25. A method for generating liquid oxygen in a home from a home liquid oxygen ambulatory system having an oxygen concentrator, a condenser, a cryocooler, a recuperator and a storage dewar, comprising:

(a) generating a gaseous supply of oxygen, which includes some trace impurities, using the oxygen concentrator;

(b) splitting off at least a portion of the gaseous supply to be liquefied;

(c) cooling said supply of oxygen using the condenser and cryocooler to transform the gaseous oxygen to liquid oxygen;

(d) condensing less than all of the gaseous oxygen supply flowing into the condenser;

(e) freezing out the trace impurities of the gaseous supply of oxygen and venting the excess gaseous oxygen with said recuperator;

(f) storing the liquid oxygen in the storage dewar; and (g) periodically removing accumulated frozen impurities on said recuperator by boiling-off any stored liquid oxygen and then flow purging the system until the system has reached room temperature.

26. A generally vertically oriented, gravity assisted condenser for use with a refrigerating mechanism to liquefy gaseous oxygen in a home liquid oxygen ambulatory system, comprising:

a generally vertically oriented tubular member adapted to conduct heat axially to said refrigerating mechanism, the tubular member having a geometric center and outer and inner surfaces, at least one of said outer and inner surfaces having a plurality of generally vertically oriented flutes and convex fins adapted to increase the condensation rate per unit area by thinning the liquid film and drain the condensate to keep the condensate from flooding the condensation surfaces, wherein the flutes and convex fins are circumferentially spaced with respect to each other and not radially aligned with each other relative to the geometric center of the tubular member.

27. The condenser of claim 26, wherein the fins have a hyperbolic cosine profile.

28. The condenser of claim 26, wherein said plurality of generally vertically oriented flutes and convex fins are located on said inner surface.

29. The condenser of claim 26, wherein said plurality of generally vertically oriented flutes and convex fins are located on both said outer and inner surfaces.

30. A generally vertically oriented, gravity assisted condenser for use with a refrigerating mechanism to liquefy gaseous oxygen in a home liquid oxygen ambulatory system, comprising:

a generally vertically oriented tubular member adapted to conduct heat axially to said refrigerating mechanism, the tubular member having outer and inner surfaces, at least one of said outer and inner surfaces includes means for enhancing the condensation rate per unit area by maintaining a small liquid film thickness on the condensation surfaces, said condensation enhancing means including a plurality of generally vertically oriented flutes and convex fins located on both said outer and inner surfaces.

* * * * *